US009248115B2

(12) United States Patent
Rovati et al.

(10) Patent No.: US 9,248,115 B2
(45) Date of Patent: Feb. 2, 2016

(54) SILIBININ COMPONENT FOR THE TREATMENT OF HEPATITIS

(71) Applicant: MADAUS GmbH, Cologne (DE)

(72) Inventors: Lucio Claudio Rovati, Monza (IT); Massimo Maria D'Amato, Monza (IT); Ulrich Mengs, Roesrath (DE); Ralf-Torsten Pohl, Speyer (DE); Peter Ferenci, Vienna (AU)

(73) Assignee: MADAUS GMBH, Cologne (DE)

( * ) Notice: Subject to any disclaimer, the term of this patent is extended or adjusted under 35 U.S.C. 154(b) by 23 days.

(21) Appl. No.: 13/871,045

(22) Filed: Apr. 26, 2013

(65) Prior Publication Data

US 2013/0236420 A1 Sep. 12, 2013

Related U.S. Application Data

(62) Division of application No. 12/742,916, filed as application No. PCT/EP2008/009659 on Nov. 14, 2008, now abandoned.

(60) Provisional application No. 60/988,168, filed on Nov. 15, 2007.

(30) Foreign Application Priority Data

Nov. 15, 2007 (EP) ..................... 07022187
Mar. 25, 2008 (EP) ..................... 08005459

(51) Int. Cl.
| | |
|---|---|
| *A61K 31/35* | (2006.01) |
| *A61K 31/335* | (2006.01) |
| *A61K 31/357* | (2006.01) |
| *A61K 31/7056* | (2006.01) |
| *A61K 38/21* | (2006.01) |
| *A61K 45/06* | (2006.01) |

(52) U.S. Cl.
CPC ........... *A61K 31/357* (2013.01); *A61K 31/7056* (2013.01); *A61K 38/21* (2013.01); *A61K 45/06* (2013.01)

(58) Field of Classification Search
USPC ................................. 514/449, 452
See application file for complete search history.

(56) References Cited

U.S. PATENT DOCUMENTS

| | | | |
|---|---|---|---|
| 4,061,765 A | 12/1977 | Madaus et al. | |
| 4,764,508 A | 8/1988 | Gabetta et al. | |
| 4,871,763 A * | 10/1989 | Madaus et al. | 514/452 |
| 5,714,473 A | 2/1998 | Lentzen et al. | |
| 6,849,254 B1 * | 2/2005 | Brass et al. | 424/85.7 |
| 2005/0123628 A1 | 6/2005 | Zabrecky | |

FOREIGN PATENT DOCUMENTS

| | | |
|---|---|---|
| CN | 1762345 A | 4/2006 |
| CN | 1839288 A | 9/2006 |
| CN | 1839822 A | 10/2006 |
| CN | 1990484 A | 7/2007 |
| CN | 101244059 | 8/2008 |
| CN | 101439018 A | 5/2009 |
| EP | 0 422 497 B1 | 4/1991 |
| GB | 2 167 414 | 5/1986 |
| JP | 61143377 A | 7/1986 |
| JP | 05-271071 | 10/1993 |
| JP | 2002504514 A | 2/2002 |
| WO | 9955326 A1 | 11/1999 |
| WO | 00/32177 A3 | 6/2000 |
| WO | 02/067853 | 9/2002 |
| WO | 02/067853 A2 | 9/2002 |
| WO | 02/067853 A3 | 9/2002 |
| WO | 03/090741 A1 | 11/2003 |

OTHER PUBLICATIONS

Ciriaci, A.M. et al., Gastroenterology vol. 112, No. 4, Supplemental p. A1246. Published 1997.*
Davis-Searles, P. R. et al., Cancer Research vol. 65, pp. 4448-4457. Published 2005.*
V. Schonfeld, J. et al. Cellular and Molecular Life Sciences vol. 53, pp. 917-920. Published 1997.*
Schumann, J. et al. Journal of Hepatology vol. 39 pp. 333-340. Published 2003.*
Mayer, K.E. et al., Journal of Viral Hepatitis. vol. 12, pp. 559-567. Published 2005.*
Schumann et al (Journal of Hepatology vol. 39, pp. 333-340, published 2003).*
Mengs, U. et al. Current Pharmaceutical Biotechnology vol. 13, pp. 1964-1970. Published 2012.
Schumann, J., et al., Silibinin protects mice from T-cell dependent liver injury. Journal of Hepatology 39,333-340. Published 2003.
Mayer, K. E., et al., Silymarin treatment of viral hepatitis: a systematic review. Journal of Viral Hepatitis, vol. 12, pp. 559-567. Published 2005.
Reagan-Shaw, S. et al., Dose translation from animal to human studies revisited. FASEB J. 22, 659-661, Published Mar. 2007.
Verma et al.; "Complementary and Alternative Medicine in Hepatology: Review of the Evidence of Efficacy"; Clinical Gastroenterology and Hepatology 2007;5:408-416.
Waris et al.; "Hepatitis C Virus (HCV) Constitutively Activates STAT-3 via Oxidative Stress: Role of STAT-3IN HCV Replication;" Journal of Virology 2005;79:1569-1580.

(Continued)

*Primary Examiner* — Paul Zarek
*Assistant Examiner* — George W Kosturko
(74) *Attorney, Agent, or Firm* — Miles & Stockbridge PC

(57) ABSTRACT

The invention relates to the use of a silibinin component for the production of a medicament that is adapted for parenteral administration for the treatment of viral hepatitis, preferably of hepatitis B or C, in particular for the reduction of the virus load. The medicament preferably contains no silidianin and/or no silichristin and/or no isosilibinin.

13 Claims, 14 Drawing Sheets

(56) References Cited

OTHER PUBLICATIONS

Weislow et al.; New Soluble-Formazan Assay for HIV-1 Cytopathic Effects: Application to High-Flux Screening of Synthetic and Natural Products for Aids-Antiviral Activity; J. Natl. Cancer Inst. 1989;81:577-586.
Wen et al.; "Pharmacokinetics and Metabolic Profile of Free, Conjugated, and Total Silymarin Flavonolignans in Human Plasma After Oral Administration of Milk Thistle Extract"; The American Society for Pharmacology and Experimental Therapeutics 2008;36(1) 65-72.
Zhang J.Q., et ai, Preparation and Characterization of Solid Nanoparticles Containing Silibinin, Informa Healthcase, 2007, pp. 381-387.
Song Y, et ai, Preparation and properties of silybin-phospholipid complex, Pharmazie, Jan. 2008, Abstract.
Encyclopedia of Medicaments, 2008, p. 805.
Bartenschlager; "Hepatitis C Virus Replicons: Potential Role for Drug Development"; Nat. Revs. Drug Discovery 2002;1 :911-917.
Bauer et al.; "Lehrbuch Der Pharmazeutischen Technologie" 232-241 (Wissenschaftliche Verlagsgesellschaft MBH Stuttgart 1999).
Chavez; "Treatment of Hepatitis C With Milk Thistle"; Journal of Herbal Pharmacotherapy, vol. 1 (3) 2001; 1( 3):79-90.
Herbert P. Fiedler, "Lexikon der Hilfsstoffe fUr Pharmazie, Kosmetik and angrenzende Gebiete" (Editio Cantor Verlag Aulendorf 2002).
Gabbay et al.; "Antioxidant Therapy for Chronic Hepatitis C After Failure of Interferon: Results of Phase II Randomized, Double-Blind Placebo Controlled Clinical Trial"; World J. Gastroenterol; 2007; 13(40):5317-5323.
Gordon et al.; "Effects of Silybum Marianum on Serum Hepatitis C Virus RNA, Alanine Aminotransferase Levels and Well-Being in Patients With Chronic Hepatitis C"; J. Gastroenterol Hepatol. 2006; 21(1 PT 2):275:280.
Hoofnagle, J.H.; "Hepatitis C: The Clinical Spectrum of Disease" Hepatology. 1997;26:15S-20S.
Kim et al.; "Complete Isolation and Characterization of Silybins and Isosilybins From Milk Thistle (Silybum Marianum)"; Org. Biomol. Chem. 2003;1 :1684-1689.
Kroll et al.; "Milk Thistle Nomenclature: Why It Matters in Cancer Research and Pharmacokinetic Studies"; Integrative Cancer Therapies 2007;6(2):110-119.
Lee et al.; Molecular Structure and Stereochemistry of Sil Ybin A, Sil Ybin B, Isosil Ybin A, and Isosilybin B, Isolated From Silybum Marianum (Milk Thistle); J. Nat. Prod. 2003;66:1171-1174.
Mayer et al.; "Silymarin Treatment of Viral Hepatitis: A Systematic Review"; Journal of Viral Hepatitis, 2005;12:559-567.
Memon et al.; "Hepatitis C: An Epidemiological Review"; Journal of Viral Hepatitis, 2002;9:84-100.
Polyak et al; "Inhibition of T-Cell Inflammatory Cytokines, Hepatocyte NF-KB Signaling, and HCV Infection by Standardized Silymarin"; Basic-Liver, Pancreas, and Biliary Tract; Gastroenterology 2007; 132: 1925-1936.
Rainone; "Milk Thistle"; Am Fam Physician 2005;72(7):1285-1288.
Saller et al.; "The Use of Silymarin in the Treatment of Liver Diseases"; Drugs 2001: 61 (14 ):2035-2063.
Simmonds et al.; "Consensus Proposals for a Unified System of Nomenclature of Hepatitis C Virus Genotypes"; Hepatology 2005;42:962-973.
Stauber et al; "Drugs in Development for Hepatitis C"; Drugs 2008;68(10):1347-1359.
Tanamly, MD et al.; Randomised Double-B;Inded Trial Evaluating Silymarin for Chronic Hepatitis C in an Egyptian Village: Study Description and 12-Month Results; Dig Liver Dis. Nov. 2004; 36(11):752-759.
Tan et al; "Hepatitis C Therapeutics: Current Status and Emerging Strategies"; Nat Rev Drug Discov. 2002;1(11):867-881.
Vailati et al.; "Randomized Open Study of the Dose-Effect Relationship of a Short Course of IDB 10161N Patients With Viral or Alcoholic Hepatitis"; Fitoterapia, 1993;64(3)219-228.
Varghese et al.; "Silibinin Efficacy Against Human Hepatocellular Carcinoma"; CLiN. Cancer Res. 2005;11 (23):8441-8448.

Boigk et al.; Silymarin Retards Collagen Accumulation in Early and Advanced Biliary Fibrosis Secondary to Complete Bile Duct Obliteration in Rats; Hepatology 1997;26:643-649.
Buzzelli et al.; "A Pilot Study on the Liver Protective Effect of Silybinphosphatidylcholine Complex (IDB1016) in Chronic Active Hepatitis"; Int J CLiN Pharmacol, Ther, Tox; 1993;31 (9):456-460.
Conjeevaram et al.; "Peginterferon and Ribavirin Treatment in African American and Caucasian American Patients With Hepatitis C Genotype 1"; Gastroenterology; 2006; 131:4 70-4 77.
Dehmlow et al.; "Inhibition of Kupffer Cell Functions as an Explanation for the Hepatoprotective Properties of Silibinin"; Hepatology; 1996;23:749-754.
Di Bona et al.; "Oxidative Stress Inhibits IFN-A-Induced Antiviral Gene Expression by Blocking the JAK-STAT Pathway"; Journal of Hepatology 2006;45:271-279.
Ding et al.; "Determination of Active Component in Silymarin by R-P-LC and LC/MS"; Journal of Pharmaceutical and Biomedical Analysis; 2001 ;26:155-161.
Falasca et al.; "Treatment With Silybin-Vitamin E-Phospholipid Complex in Patients With Hepatitis C Infection"; Journal of Medical Virology 2008;80:1900-1906.
Federico et al.; A New Silybin-Vitamin E-Phospholipid Complex Improves Insulin Resistance and Liver Damage in Patients With Non-Alcoholic Fatter Liver Disease: Preliminary Observations; Gut. 2006;55(6):901-902.
Ferenci et al.; "Randomized Controlled Trial of Silymarin Treatment in Patients With Cirrhosis of the Liver"; J Hepatol 1989;9:105-113.
Fried et al.; "Peginterferon ALFA-2A Plus Ribavirin for Chronic Hepatitis C Virus Infection"; N. Engl. J. Med. 2002;347(13):975-982.
Hadziyannis et al.; "Peginterferon-A2AAND Ribavirin Combination Therapy in Chronic Hepatitis C" 2004 American College of Physicians; Ann. Inter. Med. 2004;140:346-255.
Hruby et al.; "Chemotherapy of Amanita Phalloides Poisoning With Intravenous Silibinin"; Human Toxicol. 1983;2:183-195.
Hwang et al.; "Hepatitis C Virus NS5B Protein Is a Membrane-Associated Phosphoprotein With a Predominantly Perinuclear Localization"; Virology 1997;227:439-446.
Janssen et al.; "Differential Induction of C-FOS, C-JUN, and Apoptosis in Lung Epithelial Cells Exposed to ROS or RNS"; Am J Physiol. 1997;273(4 Pt 1):L789-L796.
Koike et al.; "Oxidative Stress and Hepatitis C Viral Infection"; Hepatology Research 2006;34:65-73.
Letschert et al.; "Molecular Characterization and Inhibition of Amanitin Uptake Into Human Hepatocytes"; Toxicology Sciences; 2006;91 (1): 140-149.
Lucena et al.; "Effects of Silyarin MZ-80 on Oxidative Stress in Patients With Alcoholic Cirrhosis"; Int J CLiN Pharm Ther 2002;40(1 ):2-8.
Manns et al.; Peginterferon ALFA-2B Plus Ribavirin Compared With Interferon ALFA-2B Plus Ribavirin for Initial Treatment of Chronic Hepatitis C: A Randomised Trial; Lancet 2001 ;358:958-965.
Mira et al.; "Scavenging of Reactive Oxygen Species by Silibinin Dihemisuccinate" Biochem. Pharmacal. 1994;48(4)753-59.
Okuda et al.; Mitochondrial Injury, Oxidative Stress, and Antioxidant Gene Expression Are Induced by Hepatitis C Virus Core Protein; Gastroenterology; 2002;122:366-375.
Pietrangelo et al.; "Antioxidant Activity of Silybin In Vivo During Long-Term Iron Overload in Rats"; Gastroenterology; 1995;109:1941-1949.
Roehm et al.; "An Improved Colorimetric Assay for Cell Proliferation and Viability Utilizing the Tetrazolium Salt XTT"; Journal of Immunological Methods 1991;142:257-265.
Scudiero et al.; "Evaluation of a Soluable Tetrazolium/Formazan Assay for Cell Growth and Drug Sensitivity in Culture Using Human and Other Tumor Cell Lines"; Cancer Research 1998;48:4827-4833.
Seeff et al.; "Complementary and Alternative Medicine in Chronic Liver Disease"; Hepatology; 2001 ;34(3):595-603.
Sonnenbichler et al.; "Biochemical Effects of the Flavonolignane Silibinin on RNA, Protein and DNA Synthesis in Rat Livers" Prog Clin Bioi Res. 1986;213:319-31.
Strade et al.; "Diagnosis, Management, and Treatment of Hepatitis C" Hepatology 2004;39 (4):1147-1171.

(56) References Cited

OTHER PUBLICATIONS

Torres, MD, et al.; "Does Silybum Marianum Play a Role in the Treatment of Chronic Hepatitis C?" Puerto Rico Health Sciences Journal. 2004;23(2):69-74.
Polyak Stephen J et al.: "Inhibition of T-cell inflammatory cytokines, hepatocyte NF-kappa B signaling, and HCV infection by standardized silymarin" Gastroenterology, vol. 132, No. 5, May 2007, pages ISSN: 0016-5085.
Chavez M. L: "Treatment of Hepatitis C With Milk Thistle?" Journal of Herbal Pharmacotherapy, Haworth Herbal Press, Binghamton, US, vol. 1, No. 3, 2001, pp. 79-90, XP009047629 ISSN: 1522-8940.
Vailati A et al: "Randomized open study of the dose-effect relationship of a short course of IdB 1016 in patients with viral or alcoholic hepatitis" Fitoterapia, vol. 64, No. 3, 1993, pp. 219-228, XP008090601 ISSN: 0367-326X.
Ciriaci A M et al: "Interferon alfa versus silibinin plus interferon in chronic hepatitis C previously resistant to interferon: A randomized trail" Gastroenterology, Elsevier, Philadelphia, PA, US, vol. 112, No. 4 Suppl, 1997, p. A1246, XP008090606 ISSN: 0016-5085.
Gendraul T J L et al: "[Effect of an water-soluble derivative of silymarin on morphological and functional alterations of mouse hepatocytes induced by Frog Virus 3 (author's transl)]" Arzneimittel-Forschung 1979, vol. 29, No. 5, 1979, pp. 786-791, XP0081010831SSN: 0004-4172.
Feng, Zi-Ming et al: "Effects of silibinin combined with lamivudine treating the liver cirrhosis with active hepatitis B" Zhongguo Quanke Yixue, 10(8),659-661 CODEN: ZQYHAK; ISSN: 1007-9572,2007, XP008090737.
International Search Report of PCT/EP2008/009659; dated Feb. 3, 2009; (4 pgs.).
European Search Report 07022187.4; dated Apr. 23 2008; (6 pgs.).
Bantel, H. et al., Apoptosis in heatitus C virus infection. Cell and Death Differentiation. (2003) 10, 48-58.
Bayraktar, Y. et al., A comparison of the prevalence of autoantibodies in individuals with chronic hepatitis C and those with autoimmune hepatitis: the role of interferon in the development of autoimmune diseases. (1997) 417-425.
Berkson, B. M., "A Conservative triple antioxidant approach to the treatment of hepatitis C. Combination of alpha lipoic acid (thioctic acid), silymarin, and selenium: three case histories," Med Klin (Munich). 1999;94(Suppl III):84-89.
Das, S. et al., "Silymarin nanoparticle prevents paracetamol-induced hepatotoxicity," Int J Nanomedicine. 2011;6:1291-1301.
Loguercio, C. et al., "The Effect of a Silybin-Vitamin E-Phospholipid Complex on Nonalcoholic Fatty Liver Disease: A Pilot Study," Dig Dis Sci. 2007;52(9):2387-2395.
Trappoliere, M. et al., "[Effects of a new pharmacological complex (Sylbin and Vitamin E Phospholipids on some markers of metabolic syndrome and of a liver fibrosis in patients with non-alcoholic fatty liver disease: A preliminary open pilot study]," Minerva Gastroenterol Dietol. 2005;51(2)193-199.

* cited by examiner

Figure 11
Silibinin A
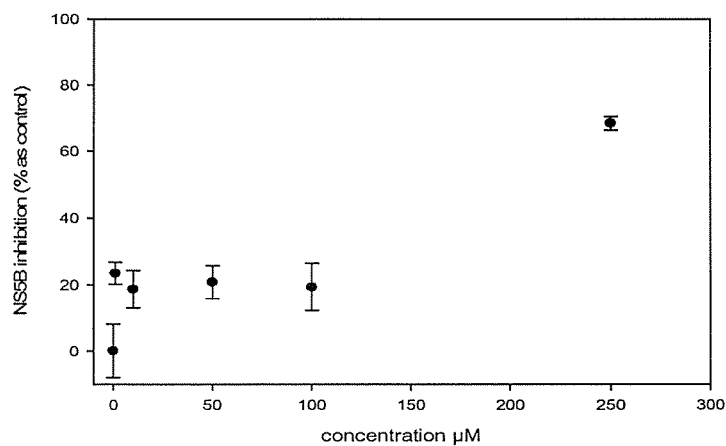
Silibinin B
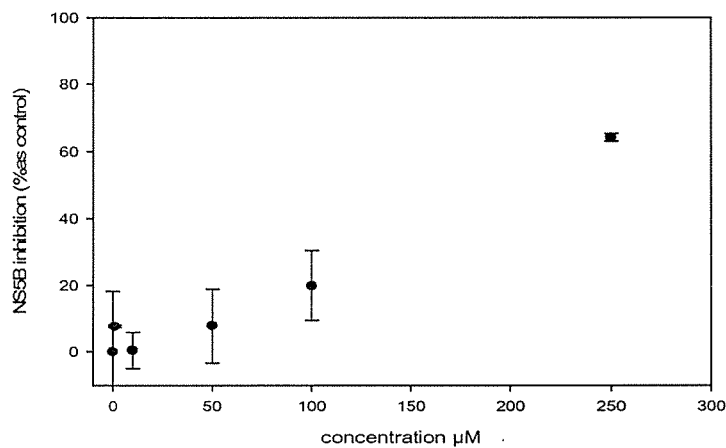
Isosilibinin A
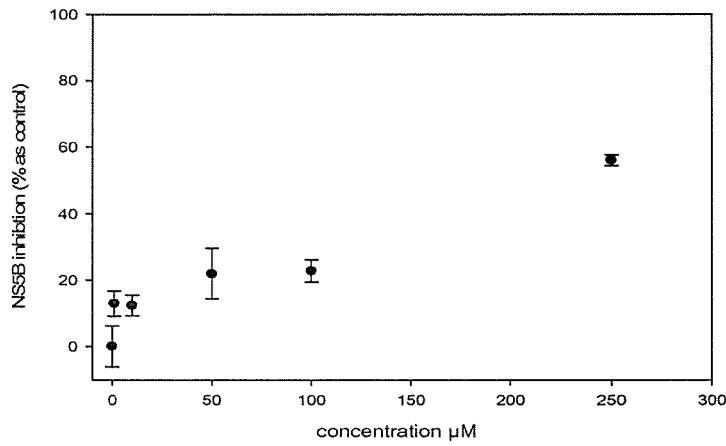

Figure 11 (continued)
Isosilibinin B
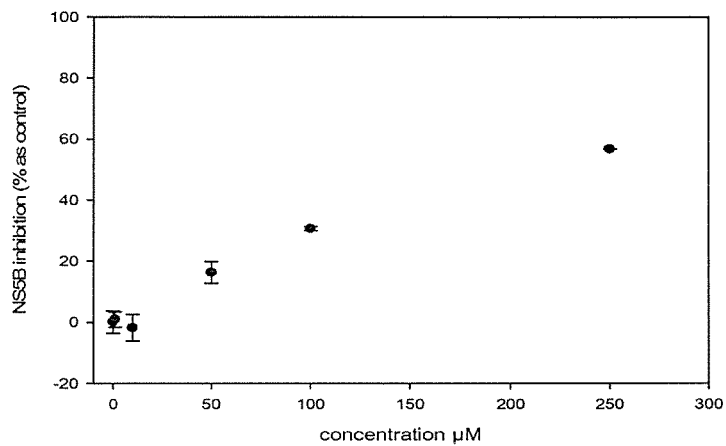
Silichristin
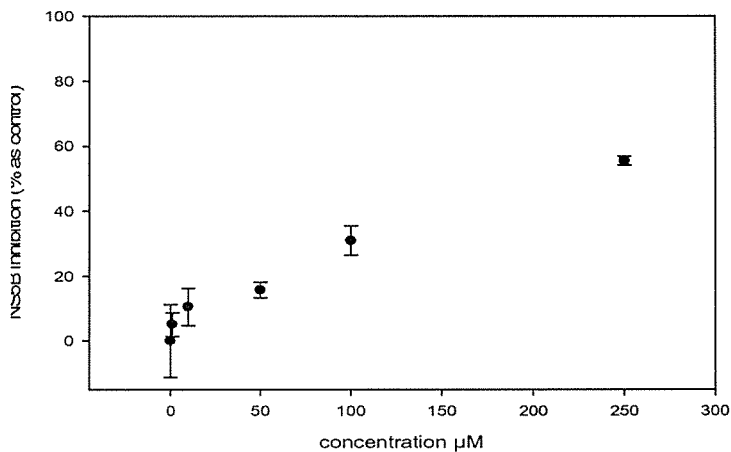
Silidianin
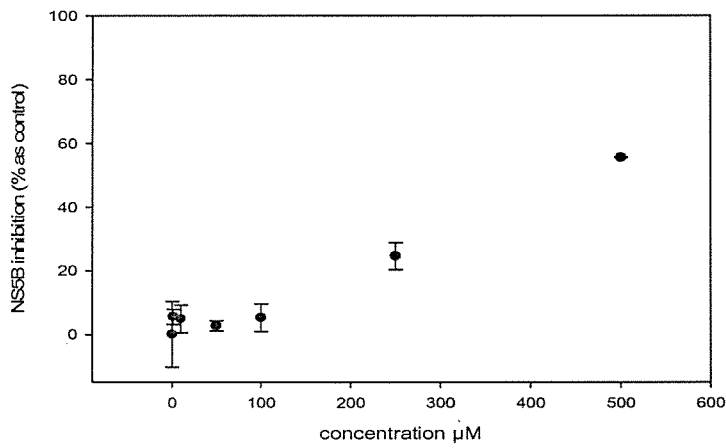

SILIBININ COMPONENT FOR THE TREATMENT OF HEPATITIS

This application is a Divisional application of U.S. application Ser. No. 12/742,916, filed Mar. 31, 2011, which is a National Stage of PCT/EP2008/009659, filed Nov. 14, 2008, which claims priority to U.S. Provisional Application 60/988,168, filed Nov. 15, 2007, which claims priority to European Application 07022187.4, filed Nov. 15, 2007 and European Application No. 08055459.6, filed Mar. 25, 2008. All of these are hereby incorporated by reference in their entireties.

This invention relates to the use of a silibinin component for the production of a medicament for the treatment of viral hepatitis, preferably hepatitis B or C, in particular for the reduction of the virus load. Preferably, the medicament is adapted for parenteral administration. Preferably, the silibinin component is a silibinin ester.

Silibinin {3,5,7-trihydroxy-2-(3-(3-hydroxy-4-methoxyphenyl)-2-(hydroxymethyl)-2,3-dihydrobenzo[b][1,4]-dioxin-6-yl)chroman-4-one; or according to Ph. Eur. (2R,3R)-3,5,7-trihydroxy-2-[(2R,3R)-3-(4-hydroxy-3-methoxyphenyl)-2-(hydroxymethyl)-2,3-dihydro-1,4-benzo-dioxin-6-yl]-2,3-dihydro-4H-1-benzopyran-4-one} is the main constituent of silymarin and the main flavonoid extracted from milk thistle (Silybum marianum Gaertneri).

Silibinin has the following structure:

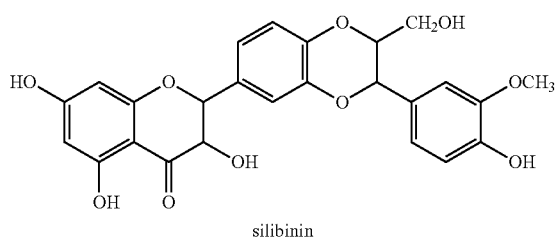 [SMILES: COc1cc(C2Oc3cc(C4Oc5cc(O)cc(O)c5C(=O)C4O)ccc3OC2CO)ccc1O]

silibinin

The diastereomers silibinin A and silibinin B are distinguished in the literature:

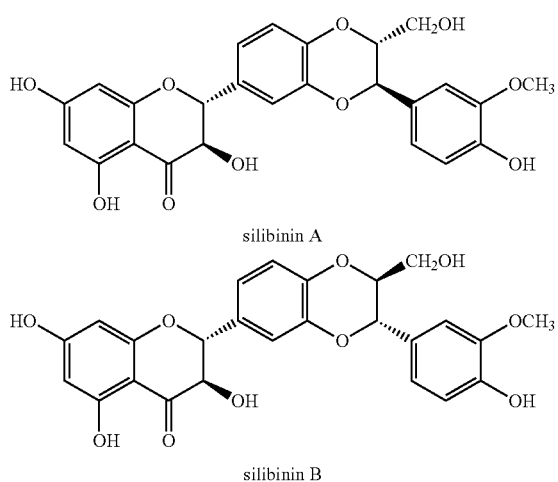

silibinin A silibinin B

Silibinin is the major constituent of silymarin (in a 50:50 mixture of Silybin A and Silybin B). Further constituents include isosilibinin (isosilybin A and isosilybin B), silidianin (silydianin), silichristin (silychristin), isosilychristin, taxifolin and others. Methods for isolating silibinin are known from the prior art (e.g., U.S. Pat. No. 4,871,763).

Silibinin and silymarin have been investigated and described in detail. In this connection, reference can be made, for example, to N-C Kim et al., Org. Biomol. Chem. 2003, 1, 1684-9; DYW Lee et al., J. Nat. Prod. 2003, 66, 1171-4; DJ Kroll et al., Integrative Cancer Therapies, 2007, 6, 110-9; Z Wen et al., DMD Fast Forward, doi:10.1124/dmd.107.017566; and U.S. Pat. No. 4,871,763.

Silybum marianum has a history as medical plant for almost 2 millennia. Silymarin, the seed extract of milk thistle is an ancient herbal remedy used to treat a range of liver and gallbladder disorders, including hepatitis, cirrhosis, and as a hepatoprotectant against poisoning from wild mushroom, alcohol, chemical, and environmental toxins. The mode of action of silymarin is diverse. The largest randomized, controlled trial performed in the 1970ies indicated that long-term treatment with silymarin may decrease mortality in patients with cirrhosis (P Ferenci et al., J Hepatol 1989, 9, 105-13). Nevertheless, the role of the drug for treatment of liver diseases remains controversial (S Verma et al., Clinical Gastroenterology and Hepatology 2007, 5, 408-16; F Rainone, Am Fam Phys 2005, 72(7), 1285-8). Part of this uncertainty is due to the limited data on its pharmacokinetics and optimal dosing regimens. Silymarin is poorly water soluble and oral preparations have limited bioavailability.

Pharmaceutical applications of silibinin are also known. Silibinin has strong antioxidative properties (cf. A Pietrangelo et al., Gastroenterology 1995, 109, 1941-49; MI Lucena et al., Int J Clin Pharmacol Ther 2002, 40, 2-8; and L Mira et al., Biochem Pharmacol 1994, 48, 753-9) and antifibrotic properties (cf. G Boigk et al., Hepatology 1987, 26, 643-9; and C Dehmlow et al., Hepatology 1996, 23, 749-54) which makes it a potentially useful drug for treatment of chronic liver diseases. The pure substance silibinin is administered intravenously, for example, in the case of liver poisoning by the death cap (amanitine, phalloidin) in order to keep the liver from further damage (cf. K Hruby et al., Hum Toxicol 1983, 2, 138-195). The effect in mushroom poisoning is in part explained by the stimulation of nucleolar polymerase A which increases ribosomal protein synthesis and inhibits lipid peroxidation (J Sonnenbichler et al., Prog Clin Biol Res. 1986, 213, 319-31). Clinical tests also show success in the prevention and treatment of certain types of cancer (L Varghese et al. Clin Cancer Res 2005, 11(23), 8441-7; K Letschert et al., Toxicological Sciences 2006, 91, 140-9).

A silibinin ester is marketed as an infusion solution, for example, under the name Legalon® SIL in the Federal Republic of Germany.

Viral hepatitis refers to infections that affect the liver and are caused by viruses. It is a major public health issue worldwide. Not only does viral hepatitis carry a high morbidity, but it also stresses medical resources and can have severe economic consequences. The majority of all viral hepatitis cases are preventable.

Viral hepatitis includes five distinct disease entities, which are caused by at least five different viruses. Hepatitis A and hepatitis B (infectious and serum hepatitis, respectively) are separate diseases and both can be diagnosed by a specific serologic test. Hepatitis C and E comprise a third category, each a distinct type, with Hepatitis C parenterally transmitted, and hepatitis E enterally transmitted. Hepatitis D, or delta hepatitis, is another distinct virus that is dependent upon hepatitis B infection. This form of hepatitis may occur as a super-infection in a hepatitis B carrier or as a co-infection in an individual with acute hepatitis B.

Hepatitis C is an infectious disease in humans, which is caused by the hepatitis C virus (HCV). HCV infection can lead in its course to severe liver damage, e.g. inflammation of the liver parenchyma, fibrosis of the liver, cirrhosis of the liver and carcinoma of the liver. In over 80% of the infected patients, HCV infection becomes chronic. The transmission of HCV usually takes place parenterally via the blood.

It is estimated that about 170 million people worldwide are infected with the hepatitis C virus (HCV). The infected patients can be asymptomatic for decades, until the development of cirrhosis of the liver and/or hepatocellular carcinomas finally occurs. Approximately 40-50% of the liver transplants in the United States are based on HCV infections. Six genotypes of HCV have been identified (HCV1-HCV6), which differ in their geographical spread and in their response to medicinal therapies.

HCV proteins have been shown to induce activation of STAT-3 via oxidative stress and $Ca^{2+}$ signalling (K Koike et al., Hepatol Res 2006; 34: 65-73; G Waris et al., J Virol 2005, 79, 1569-80) as well as lipid peroxidation products and antioxidant gene expression (M Okuda et al., Gastroenterology 2002, 122, 366-375). It appears that the balance of the oxidative and reductive potentials within the cell (cellular redox state) has profound consequences on signal transduction pathways (YM Janssen et al., Am J Physiol 1997, 273:789-96) including impaired IFN-alpha signalling (D Di Bona et al., J. Hepatol. 2006, 45, 271-9).

HCV infection is divided according to ICD10 (WHO, Version 2007) into acute (817.1) and chronic hepatitis C (B18.2).

HCV is one of the most important causes of the developments of acute or chronic hepatitis. The clinical course of the disease, however, might be very different and subject to a high variability. It is thus not possible to speak about a typical course of the disease, since the HCV infection is essentially manifested by a broad clinical spectrum, i.e. by variable symptoms, different clinical pictures and variable hepatic and extrahepatic secondary diseases.

In approximately 20% of the patients with acute hepatitis, the inflammation of the liver is to be attributed to an HCV infection. In the acute phase, however, hepatitis C usually proceeds asymptomatically and it is therefore not diagnosed in approximately 85% of the cases. In some cases, only non-specific symptoms of a putatively flu-like syndrome occur. Usually, the infection is not manifested during the acute phase.

Hepatitis C becomes chronic in about 85% of the patients with acute HCV infection. This high chronification rate appears to be a result of the high virus variability of the HCV; i.e. the gene which codes for the coat of the HCV is subject to a high mutation rate. Because of the high virus variability, and in particular the high variability of the antigenic epitope of the HCV, the mutated HCV escapes recognition by the human immune system. In about 25% of the patients, as a result of chronic liver inflammation the formation of cirrhosis of the liver occurs with an increased risk of the development of carcinoma of the liver (cf., for example, J. H. Hoofnagle, Hepatology 1997, 26, Suppl. 1, 15S-20S; M. I. Memon et al., Journal of Viral Hepatitis 2002, 9, 84-100; S. L. Tan et al., Nature Reviews, Drug Discovery 2002, 1, 867-81).

Patients who are infected with HCV usually receive a medicinal standard combination therapy consisting of pegylated interferon-α2a or interferon-α2b and ribavirin. In HCV infections due to genotype 2 or 3 (HCV2 or HCV3 infections), this combination therapy is carried out for 24 weeks. In HCV infections due to genotype 1 (HCV1) HCV1-positive patients the combination therapy is carried out for 48 weeks. Many of the HCV-infected patients, however, discontinue the treatment because of the side effects which occur and/or the low compliance on account of the parenteral administration and the long treatment period. Moreover, only about 50% of the patients having HCV1 infection achieve a long lasting treatment result, i.e. the remainder does not respond (cf., for example, RET Smith, Nature Reviews, Drug Discovery, 2006, 5, 715). Pegylated interferon plus ribavirin therapy for hepatitis C virus fails in approximately half of genotype 1 patients. Treatment failure occurs either by nonresponse (minimal declines in viral titer) or relapse (robust initial responses followed by rebounds of viral titers during or after therapy). These different patterns could be affected by many factors including host genetics, immune response, and viral genetic differences (cf. MW Fried et al., New England Journal of Medicine 2002, 347, 975-82; HS Conjeevaram et al., Gastroenterology 2006, 131, 470-7; MP Manns et al., Lancet 2001, 358, 958-65; DB Strader et al., Hepatology 2004, 39, 114771; SJ Hadziyannis et al., Ann Intern Med, 2004, 140, 346-55). Viral genetic differences could include either pretherapy differences or differences that arise during treatment due to viral evolution in response to the pressures applied by therapy.

New treatments are being developed, including optimization of current standard treatment with peginterferon plus ribavirin, specifically targeted antiviral therapy for HCV, novel immunomodulatory agents and treatment aimed at reducing fibrosis (cf. R. E. Stauber et al., Drugs 2008, 68(10), 1347).

Up to the present day, no vaccine against HCV is obtainable. The medicinal standard therapies are very expensive, show only a slight success in the control of the HCV infection and sometimes cause considerable side effects (S. L. Tan et al., Nature Reviews, Drug Discovery 2002, 1, 867; R. Bartenschlager, ibid. 911).

There is a need for medicaments for the treatment of viral hepatitis, in particular of hepatitis B and C.

It is an object of the invention to make available a medicament for the treatment of viral hepatitis, in particular of hepatitis B or C, which has advantages compared to the medicaments of the prior art. The medicament should if possible have no or only slight side effects and be effective, e.g., in hepatitis C patients who do not sufficiently respond to conventional combination therapy with PEG interferon/ribavirin. Furthermore, the medicament should have pronounced antiviral properties and thus lastingly decrease the virus load.

This object is achieved by the subject matter of the patent claims.

It has surprisingly been found that silibinin, its pharmaceutically tolerable salts and/or derivatives are suitable for the treatment of inflammatory, viral liver diseases, in particular of hepatitis C. Thus, in hepatitis C patients who do not respond (i.e. the so called "non-responders") to immuno-modulatory/antiviral combination therapy such as PEG interferon/ribavirin, which represents nowadays the standard treatment for hepatitis C, a significant reduction of the virus load can be achieved by administration, preferably by parenteral administration of a silibinin component. It additionally appears that the pre-treatment with the silibinin component improves the response of the patients to subsequent administration of interferon and ribavirin.

Investigations concerning the treatment of HCV infections, particularly for the inhibition of HCV infections, by administration of silymarin have been described in the prior art (cf., for example, R. Sailer et al., Drugs 2001, 61(14), 2035-63; K. E. Mayer et al., Journal of Viral Hepatitis, 2005, 12, 559-67; US 2005/0123628; S. J. Polyak et al., Gastroenterology 2007, 132, 1925-1936).

R. Sailer et al. reports that, although silymarin is not known to affect viral replication, from a pharmacological perspective it may be expected to inhibit the inflammatory and cytotoxic cascade of events triggered by the viral infection. Oral administration of a silibinin-phosphatidylcholine complex (IdB1016, 240 mg of silibinin twice daily) in a short term placebo-controlled pilot study in 20 patients with chronic active hepatitis revealed that the evolution of the AST levels was significantly reduced in the silibinin group, with no consistent differences in the other liver function tests (cf. A. Vailati et al., Fitoterapia, Volume LXIV, No. 3, 1993; G. Buzzelli et al., Int. J. Clin. Pharmacol. Ther. Toxicol. 1993, 31, 456-60).

K. E. Mayer et al. discloses that oral silymarin treatment resulted in a decrease in serum transaminases compared with baseline in four studies, and compared with placebo in only one study. However, there is no evidence that silymarin affects viral load or improves liver histology in hepatitis B or C (cf., M. L. Chavez, J. Herb. Pharmacother. 2001, 1(3), 79-90; L. B. Seeff et al., Hepatology, 2001, 34(3), 595-603). The authors conclude that silymarin compounds likely decrease serum transaminases in patients with chronic viral hepatitis, but do not appear to affect viral load or liver histology.

US2005/0123628 relates inter alia to the preparation and oral administration of compositions comprising glycyrrhizin, schisandra, ascorbic acid, L-glutathione, silymarin, lipoic acid, and D-alpha-tocopherol. These compositions are said to be useful for reducing oxidative stress and lipid peroxidation, and treating chronic liver disease, chronic hepatitis C virus infection and non-alcoholic steatohepatitis. Numerous studies have reported the hepatoprotective effects that silymarin has against a wide variety of toxins, including acetaminophen, ethanol, carbon tetra-chloride, and D-galactosamine, and against ischemic injury, radiation and iron toxicity. For the first twenty weeks of an open labeled, non-randomized, one center clinical trial, the subjects were given for oral administration two times a day a total of 1,000 mg of glycyrrhizin; three times a day a total of 1,500 mg of schisandra extract; three times a day a total of 6,000 mg of ascorbic acid; two times a day a total of 300 mg of L-glutathione; three times a day a total of 750 mg of milk thistle extract; two times a day a total of 300 mg of lipoic acid; and one time a day a total of 800 IU of D-alpha-tocopherol. For the first ten weeks of the study, the subjects were also given by intravenous (iv) injection two times a week four different parenteral compositions neither of which contained silymarin. After 10 weeks, 12.0% of the subjects, after 20 weeks 24.0% of the subjects, showed a 1 log reduction of viral load. There is no hint in US2005/0123628 that silymarin, let alone silibinin, might be responsible for this comparatively slight reduction of the viral load.

S. J. Polyak et al. compares in vitro a standardized silymarin extract (MK-001) with commercial preparations of silymarin. Both preparations are said to display antiviral activity within the used cell culture based models, although the effects of the commercial preparations were not as potent as MK-001. MK-001 inhibits expression of tumor necrosis factor-alpha in anti-CD3 stimulated human peripheral blood mononuclear cells and nuclear factor kappa B-dependent transcription in human hepatoma Huh7 cells. Moreover, MK-001 dose dependently inhibits infection of Huh7 and Huh7.5.1 cells by JFH-1 virus. MK-001 displays effects against HCV infection of isolated cells, and when combined with interferon-α, inhibited HCV replication more than interferon-α alone. To compare anti-HCV action of MK-001 with commercial preparations of silymarin, Ultrathistle® (Natural Wellness, Montgomery N.Y.) and Silybinin® (Indena SpA, Milano) are also tested. However, MK-001 is said to elicit more potent viral action than Ultrathistle® and Silybinin®. The authors conclude from these in vitro tests that, as far as the anti-HCV activity is concerned, the standardized silymarin extract MK-001 is superior over two commercial products. S. J. Polyak is silent on the parenteral administration of purified silibinin, let alone on the treatment of non-responders. Further, the findings of Polyak et al. are at odds with clinical studies that found no effect of silymarin on HCV in patients with chronic hepatitis C (MD Tanamly et al., Dig Liver Dis. 2004, 36, 752-9; E Gabbay et al., World J. Gastroenterol. 2007, 13, 5317-23).

It now has been surprisingly found that administration, particularly parenteral administration, of a preferably pure silibinin component reduces the viral load in viral hepatitis patients in vivo. Thus, the silibinin component is capable of reducing the viral load. This finding allows optimizing the dose of silibinin in the absence of further constituents of silymarin which may cause undesired side effects.

The reduction of the viral load by parenteral administration of a silibinin component is particularly surprising, since clinical studies found no effect of silymarin on HCV in patients with chronic hepatitis C (M Torres et al., P R Health Sci J 2004, 23(2), 69-74; MD Tanamly et al., Dig Liver Dis., 2004, 36:752-9; A Gordon at al., J Gastroenterol Hepatol. 2006, 21, 275-80; E Gabbay et al., World J. Gastroenterol. 2007, 13, 5317-23; and LB Seeff et al., Hepatology, 2008, 80(11), 1900-6).

M Torres et al. report about a clinical trial in which patients aged 21-65 years old with a diagnosis of chronic hepatitis C who were not using antiviral therapy were asked to participate. 34 patients were randomized to treatment with S. marianum 160 mg orally three times a week for four weeks or to no-treatment (control). The trial revealed that S. marianum has no role as an antiviral agent.

MD Tanamly et al. report about a clinical trial in which 177 patients with chronic hepatitis C virus were randomly assigned to receive either oral silymarin or multivitamin supplements. The trial revealed that the recommended dose of silymarin has no effect upon hepatitis C virus viremia.

A Gordon et al. report about a clinical trial in which 24 subjects with chronic hepatitis C were enrolled into a randomized, double-blind, placebo-controlled, crossover study. Subjects received 12 weeks of S. marianum (either 600 mg or 1200 mg/day) and placebo. Baseline biochemical, virological, psychological and quality-of-life tests were performed. Seventeen patients completed the trial. The trial revealed that mean changes in HCV RNA titers were not significantly different for subjects on S. marianum compared to those on placebo.

E. Gabbay et al. report about a clinical trial in which 100 chronic HCV infection patients who had failed in interferon treatment were enrolled and randomly assigned to receive seven different antioxidants among which silymarin capsules, 250 mg, tid. Primary end points were liver enzymes, HCV-RNA levels and histology. The trial revealed that antioxidant therapy has no effect of treatment on viral load.

LB Seeff et al. report about the Hepatitis C Antiviral Long-Term Treatment Against Cirrhosis (HALT-C) Trial, involving persons with advanced chronic hepatitis C, nonresponders to prior antiviral therapy but still willing to participate in long-term pegylated interferon treatment. No beneficial effect of silymarin was found on hepatitis C virus (HCV) RNA levels. In conclusion, silymarin users had similar HCV levels to those of nonusers.

Furthermore, it has been surprisingly found that administration, particularly parenteral administration, of a silibinin component supports conventional treatment by peginterferon/ribavirin. It was found that the silibinin component (re)activates the patients' susceptibility to conventional treatment by peginterferon/ribavirin and/or enhances the antiviral effect of conventional treatment by peginterferon/ribavirin.

BRIEF DESCRIPTION OF THE FIGURES

FIG. 11 shows data generated from in-vitro NS5B inhibition study for six purified constituents of silymarin.

Figure 1:
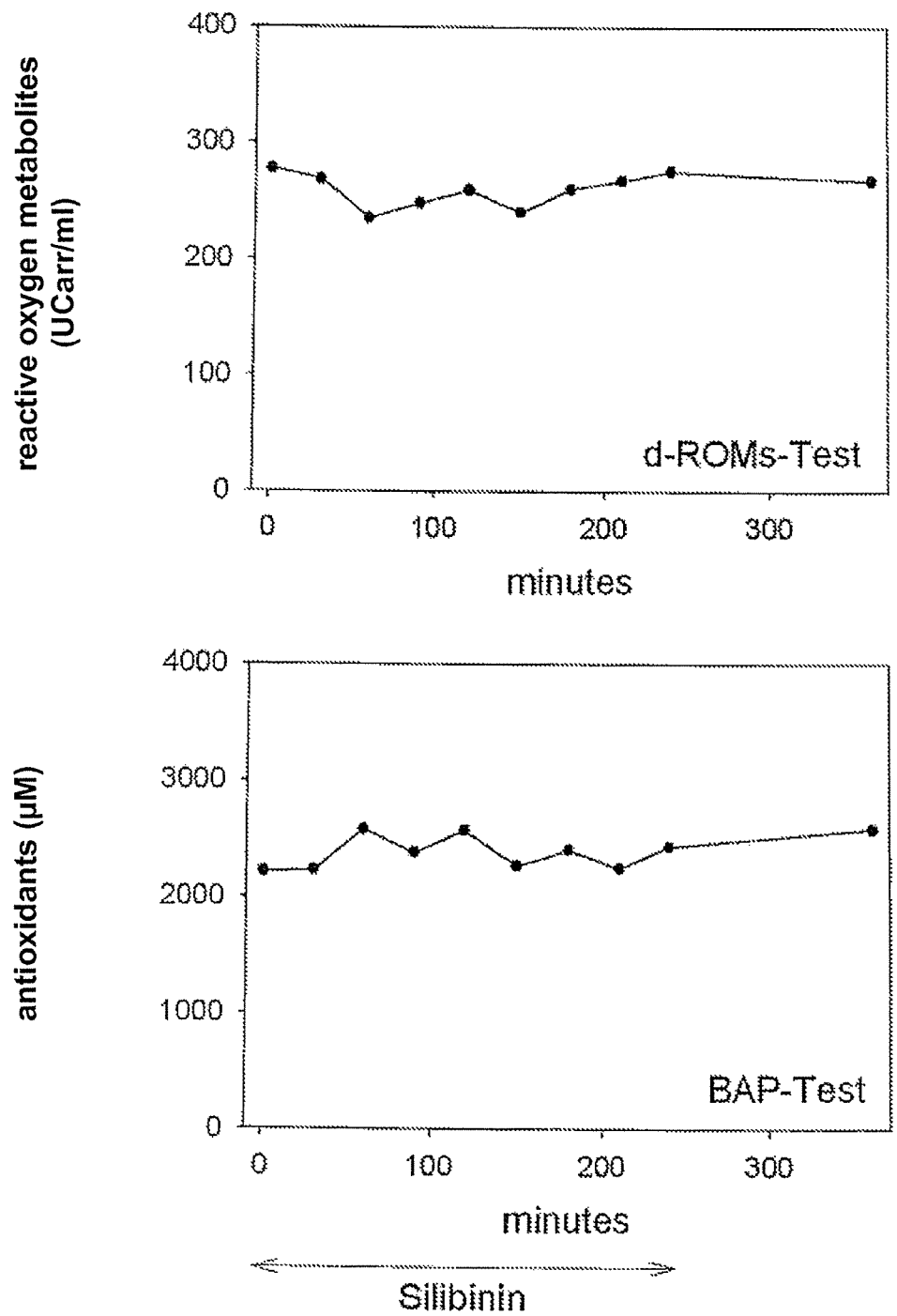
FIG. 1: Example 1, Study 1: Parameters of oxidative stress during and after infusion of 10 mg/kg silibinin component over 4 hours. (d-ROMs test=Reactive Oxygen Metabolites derived compounds, BAP test=Biological Antioxidant Potential)

The invention relates to the use of a silibinin component for the production of a, preferably virustatic or antiviral, more preferably viral load reducing medicament for the treatment of viral hepatitis, in particular of hepatitis B or C, preferably of chronic or acute hepatitis C virus infections, preferably by parenteral administration.

For the purpose of the specification, the term "medicament" preferably is synonymous to the term "medication".

In a preferred embodiment, the invention relates to the use of a silibinin component for the production of a medicament which essentially contains no silidianin and/or no silichristin and/or no isosilibinin, for the treatment of viral hepatitis, preferably of hepatitis B or C.

In a preferred embodiment, according to the invention the treatment of the viral hepatitis, in particular hepatitis B or C, is carried out by decreasing the virus load (viral load). It has been found that silibinin components are capable of reducing the viral load in hepatitis B or C patients. This is particularly surprising, as in the prior art there is no evidence that silymarin, which mixture contains a certain amount of silibinin, affects viral load or improves liver histology in hepatitis B or C (cf. K. E. Mayer et al., Journal of Viral Hepatitis, 2005, 12, 559-67).

In another preferred embodiment according to the invention, the treatment of the viral hepatitis, in particular hepatitis B or C, is carried out in patients who will undergo or have undergone liver transplantation. Patients who have undergone liver transplantation due to viral hepatitis are at risk for reestablishing viral hepatitis in the freshly transplanted liver. Usually, the virus is incompletely removed from the organism when the infected liver is removed upon surgery and the remainder of the viruses retained in the organism can re-infect the freshly transplanted liver. In chronic hepatitic C infected patients re-infection after liver transplantation occurs in 100% of the cases. As it has been surprisingly found that silibinin is capable of decreasing the virus load, the risk of re-infection after liver transplantation can be substantially reduced by administration, preferably parenteral administration, of a silibinin component.

Forms of viral hepatitis are known to the person skilled in the art.

In viral hepatitis, at present at least six different forms are definitely known: hepatitis A, B, C, D, E and G. The causative organisms of these infections are hepatotropic viruses. They belong to different virus families in each case and have a DNA or RNA genome. Transmission takes place either via the food or by the exchange of body fluids such as sperm and blood. Differences are also to be observed between the various forms with respect to the disease course and the severity of the disease. While hepatitis A and E basically occur in acute form, hepatitis B, C and D can lead to chronic courses with, in some cases, severe complications.

For the purpose of the description, the term "viral hepatitis" preferably comprises hepatitis B and C.

In a preferred embodiment, the treatment is carried out by reducing the virus load of one or more viruses selected from the group consisting of but not limited to genotypes HCV1, HCV2, HCV3, HCV4, HCV5 and HCV6, preferably HCV1.

If the genotype concerned is HCV1, the subtypes 1a, 1b, 1c, 1d, 1e, 1f, 1g, 1h, 1i, 1j, 1k and 1l are preferred. If the genotype concerned is HCV2, the subtypes 2a, 2b, 2c, 2d, 2e, 2f, 2g, 2h, 2i, 2j, 2k, 2l, 2m, 2n, 2o, 2p and 2q are preferred. If the genotype concerned is HCV3, the subtypes 3a, 3b, 3c, 3d, 3e, 3f, 3g, 3h, 3i, 3j and 3k are preferred. If the genotype concerned is HCV4, the subtypes 4a, 4b, 4c, 4d, 4e, 4f, 4g, 4h, 4i, 4j, 4k, 4l, 4m, 4n, 4o, 4p, 4q, 4r and 4t are preferred. If the genotype concerned is HCV5, the subtype 5a is preferred. If the genotype concerned is HCV6, the subtypes 6a, 6b, 6c, 6d, 6e, 6f, 6g, 6h, 6i, 6j, 6k, 6l, 6m, 6n, 6o, 6p and 6q are preferred. With respect to the nomenclature of the hepatitis C virus geno- and subtypes, reference can be made, for example, to P. Simmonds et al., Hepatology, 42, 2005, 962-73.

In a preferred embodiment, the invention relates to the use of a silibinin-component for the production of a medicament, which is preferably adapted for parenteral administration, for the treatment of viral hepatitis, preferably hepatitis C, in patients that do not respond to conventional immuno-modulatory/antiviral combination therapy such as ribavirin/interferon therapy ("non-responders") and/or in patients that partially respond to conventional immunomodulatory/antiviral combination therapy such as ribavirin/interferon therapy ("partial responders") and/or in patients that show a robust initial response followed by rebounds of viral titers during or after therapy ("relapsers").

The invention also relates to the treatment of viral hepatitis C by means of a silibinin-component, which treatment is subsequent to a conventional combination therapy by means of ribavirin/interferon. Preferably, therapy by administration of a silibinin-component starts after ribavirin/interferon therapy has failed (either initially or after a certain period of treatment).

In the connection with conventional hepatitis C therapy by administration of ribavirin/interferon, the terms "non-responders", "partial responders" and "relapsers" are known to the person skilled in the art. Nowadays, pegylated interferon plus ribavirin therapy for hepatitis C virus fails in approximately half of genotype 1 patients. Treatment failure occurs either by nonresponse (minimal declines in viral titer) or relapse (robust initial responses followed by rebounds of viral titers during or after therapy).

For the purpose of the specification, a non-responder is preferably regarded as a patient who does not show a decrease of the viral load by <2 $\log_{10}$ IU/ml (i.e., factor 100) when administering ribavirin/interferon (usually peg-interferon cc), preferably for 12 weeks. In a preferred embodiment, non-responders have viral titers declines of ≤2.1 $\log_{10}$ IU/mL and absolute titers of ≥4.62 $\log_{10}$ IU/mL at nadir.

For the purpose of the specification, a partial responder is preferably regarded as a patient who does not show a decrease of the viral load by ≥2 $\log_{10}$ IU/ml at week 12 with detectable HCV RNA at week 24.

For the purpose of the specification, a relapser is preferably regarded as a patient who has declines in viral titers of ≥2.8 $\log_{10}$ and its absolute titer transiently drops below the detection limit (2.78 $\log_{10}$ IU/mL).

For the purpose of the description, the term "medicament" is preferably synonymous with "administration form" or with "dose unit". If, for example, a medicament for oral administration is concerned, for example in the form of a tablet, this tablet is preferably the dose unit to be administered, which contains the dose of the silibinin component intended for the respective time of administration within a treatment scheme. If the dose unit comprises a single tablet, the dose unit corresponds to the administration form. It is also possible, however, for the dose unit to be divided into a number of administration forms, for example a number of tablets, which in each case contain only a partial dose, but in totality the total dose of the silibinin component, which is intended for the respective time of the administration within a treatment scheme (these tablets of the dose unit are then intended for essentially simultaneous administration).

For the purpose of the description, the term "silibinin component" preferably relates to silibinin, including all its stereoisomers, e.g., silibinin A and silibinin B, its pharmaceutically tolerable salts and/or derivatives, in particular esters. Preferred esters are derived from inorganic acids such as phosphoric acid or sulfuric acid; or organic acids such as formic acid, acetic acid, propionic acid, citric acid, malic acid, mandelic acid, and the like.

The hemiesters of dicarboxylic acids are particularly preferred, for example of malonic acid, glutaric acid, succinic acid, adipic acid, suberic acid, azelaic acid, sebacic acid, fumaric acid, maleic acid, itaconic acid, phthalic acid, terephthalic acid, isophthalic acid, etc. Preferred hemiesters are the dihemisuccinates, which can be present as free acids or as salts, for example as sodium, potassium or ammonium salts. One or more of the hydroxyl groups of the silibinin can be esterified. Preferably, 1, 2, 3, 4 or all hydroxyl groups of the silibinin are esterified.

In a preferred embodiment, the silibinin component is silibinin C-2',3-bis(hydrogensuccinate) or a physiologically acceptable salt thereof, such as the sodium salts, potassium salts, ammonium salts, and the like, as well as the mixtures thereof. Particularly preferred is the disodium salt.

Suitable esters are also gluconic acid esters.

Preferably, the silibinin component is a compound of the general formula (I)

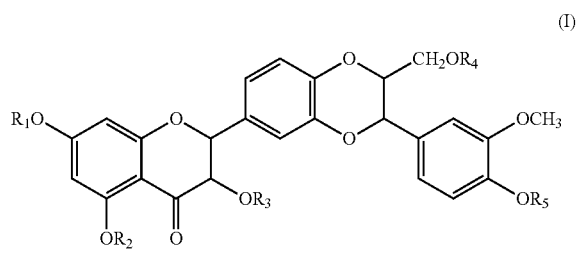

(I)

in which $R_1$, $R_2$, $R_3$, $R_4$ and $R_5$ independently of one another are selected from the group consisting of —H, —$SO_3H$, —$PO_3H_2$, —CO—$C_1$-$C_8$-alkylene-OH, —CO—$C_1$-$C_8$-alkylene-$CO_2H$, —CO—$C_1$-$C_8$-alkylene-$SO_3H$, —CO—$C_1$-$C_8$-alkylene-$OPO_3H_2$, —CO—$C_1$-$C_8$-alkylene-$PO_3H_2$, —($C_2$-$C_3$-alkylene-O)$_n$—H where n=1 to 20, —CO—$C_1$-$C_8$-alkylene-N($C_1$-$C_3$-alkyl)$_3^+X^-$, where $X^-$ is a pharmaceutically tolerable anion, or their pharmaceutically tolerable salts. Preferably, $R_1$, $R_2$ and $R_5$ are —H.

More preferably, the silibinin component of general formula (I) has the stereochemistry of the general formula (I-A) or (I-B):

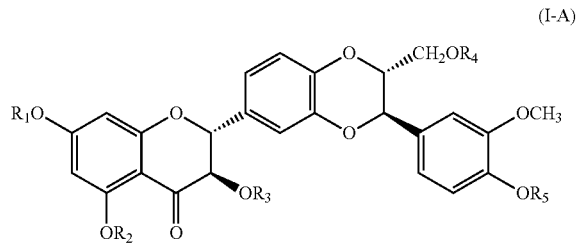

(I-A)

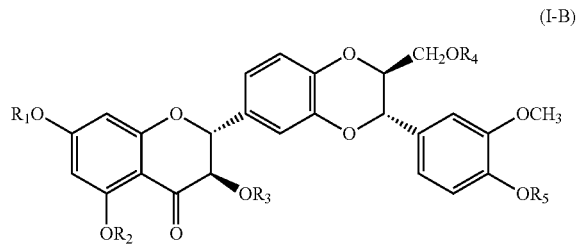

(I-B)

In a preferred embodiment, the compound of general formula (I-A) is admixed with the compound of general formula (I-B) in any relative weight ratio, e.g., 50±5:50±5. In a preferred embodiment, however, the diastereomeric excess of the compound of general formula (I-A) is at least 50% de, more preferably at least 75% de, still more preferably at least 90% de, yet more preferably at least 95% de, most preferably at least 98% de and in particular at least 99% de. In another preferred embodiment, the diastereomeric excess of the compound of general formula (I-B) is at least 50% de, more preferably at least 75% de, still more preferably at least 90% de, yet more preferably at least 95% de, most preferably at least 98% de and in particular at least 99% de.

Other preferred silibinin components are described in WO 03/090741, to which reference is made in its entirety.

Preferably, the silibinin component in pure water at room temperature has a better solubility than silibinin as such.

In a preferred embodiment, the invention relates to the use of a silibinin ester for the production of a medicament, which is preferably formulated for parenteral or oral administration, for the treatment of viral hepatitis, in particular hepatitis B or C. Preferably, the medicament essentially contains no silidianin and/or no silichristin and/or no isosilibinin.

In a preferred embodiment, the medicament is formulated for parenteral administration. Parenteral administration can be carried out, for example, subcutaneously, intravenously, intramuscularly, intraarterially, intraperitoneally, intracutaneously, intraarticularly, intrathecally, intracardially, intravitreally, retrobulbarly, intrapulmonarily and intraosseously.

Particularly preferably, the medicament is formulated for injection or infusion, in particular for intravenous or intraarterial administration.

Suitable medicaments which are suitable for injection or infusion are known to the person skilled in the art. In this connection, for example, reference can be made in its entirety to K. H. Bauer et al., Lehrbuch der Pharmazeutischen Technologie [Textbook of Pharmaceutical Technology], WVG Stuttgart 1999.

Medicaments which are suitable for injection are customarily sterile solutions, emulsions or suspensions, which are prepared by dissolving, emulsifying or suspending the active substance and optionally further excipients in water, in a suitable nonaqueous liquid which does not have to be sterile if this is justified, or in a mixture of these vehicles.

Medicaments which are suitable for infusion are customarily sterile, aqueous solutions or emulsions with water as the continuous phase.

Medicaments for injection or infusion can optionally contain further excipients. Excipients of this type are preferably solubilizers such as, for example, lecithin and poloxamer 188, substances for isotonicization such as, for example, sodium chloride, glucose and mannitol, buffers such as, for example, acetate, phosphate and citrate buffers, antioxidants such as, for example, ascorbic acid, sodium metahydrogensulfite, sodium sulfite and sodium hydrogensulfite, chelating agents such as, for example, disodium edetate, preservatives such as, for example, p-hydroxybenzoic acid esters, benzyl alcohol and chlorocresol and emulsifiers such as, for example, lecithin, fatty alcohols, sterols, sorbitan fatty acid esters, polyoxyethylene sorbitan fatty acid esters, polyoxyethylene fatty acid glycerides, polyoxyethylene fatty acid esters, polyoxyethylene fatty alcohol ethers, glycerol fatty acid esters and poloxamers.

A particularly preferred medicament is a powder for the preparation of an infusion solution comprising silibinin C-2', 3-bis(hydrogensuccinate), preferably as disodium salt, and optionally inulin as an excipient. Containers containing 598.5 mg powder of silibinin C-2',3-bis-(hydrogensuccinate) disodium salt and inulin that are adapted for the preparation of an infusion solution are commercialized in Germany under the trademark Legalon® SIL. In a preferred embodiment, the medicament according to the invention is bioequivalent to this formulation.

In another preferred embodiment, the medicament is formulated for oral administration. Preferably, the medicament is an oral administration form selected from the group consisting of tablets, capsules, sugar-coated tablets, pellets and sachets.

When administering a silibinin component via the oral route, it must be ensured that the bioavailability of the silibinin component from the oral dosage form is sufficiently high. In this respect the limiting factor is the pronounced lipophilicity of silibinin.

In a particularly preferred embodiment, the invention relates to the use of a silibinin component for the production of a medicament which is formulated for oral administration and essentially contains no silidianin and/or no silichristin and/or no isosilibinin, for the treatment of viral hepatitis, preferably of hepatitis B or C.

It seems that these further constituents of silymarin also have a physiological effect (e.g. may cause side effects), but that with respect to the treatment of viral hepatitis, silibinin (or its analogues) is most effective, particularly in reducing the viral load. Thus, when administering silymarin, i.e., a mixture of silibinin, silidianin, silichristin, isosilibinin and other constituents, the overall dose of silymarin has to be comparatively high in order to provide a particular amount of silibinin. For example, when silymarin contains, e.g., 42 wt.-% of silibinin, administration of 125 mg silymarin only provides about 52 mg of silibinin and about 73 mg of further compounds that also have a physiological effect (but not the desired effect). The risk of undesired side effects increases with the dose of a physiologically active substance. Thus, as far as the profile of undesired side effects is concerned, administration of 52 mg substantially pure silibinin is superior over administration of 125 mg silymarin having a silibinin content of 42 wt.-% (cf. T. Ding et al., "Determination of active component in silymarin by RP-LC and LC/MS", J. Pharm. Biomed. Anal. 2001, 26(1), 155-161).

The structures of silibinin (silybin), silidianin (silydianin), silichristin (silychristin) and isosilibinin (isosilybin) are displayed here below c.f. D. Y.-W. Lee et al., J. Nat. Prod. 2003, 66, 1171-4; N.-C. Kim et al., Org. Biomol. Chem., 2003, 1, 1684-9):

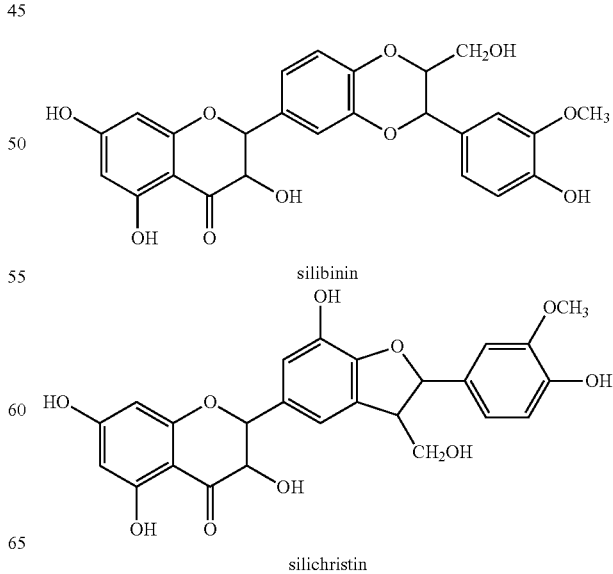

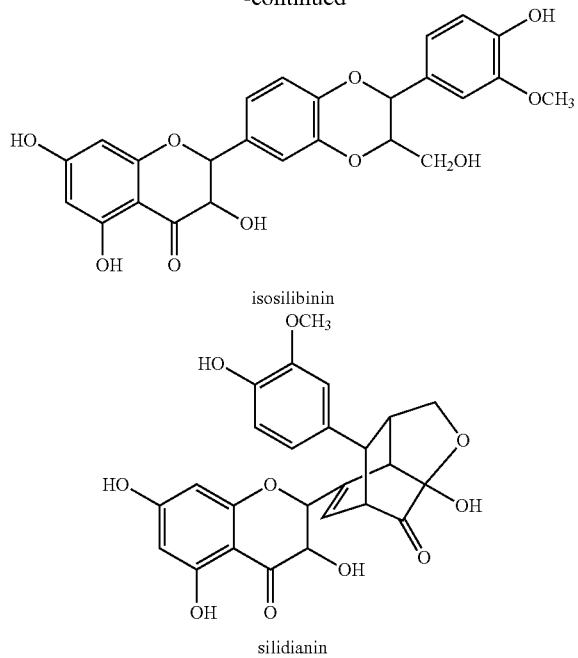

isosilibinin silidianin

Suitable administration forms which are suitable for oral administration (oral medicaments) are known to the person skilled in the art. In this connection, reference can be made in its entirety, for example, to K. H. Bauer et al., Lehrbuch der Pharmazeutischen Technologie [Textbook of Pharmaceutical Technology], WVG Stuttgart 1999.

The oral administration form is preferably selected from the group consisting of tablets, powders, pellets, granules, sugar-coated tablets, syrups, juices, solutions, effervescent powders, effervescent granules, effervescent tablets, lyophilizates and capsules. Particularly preferably, the oral administration form is a tablet, a sugar-coated tablet, granules, pellet or powder, particularly preferably a tablet.

Suitable excipients for the formulation of oral administration forms are known to the person skilled in the art. In this connection, reference can be made, for example, to H. P. Fiedler, Lexikon der Hilfstoffe für Pharmazie, Kosmetik and angrenzende Gebiete [Encyclopedia of excipients for pharmacy, cosmetics and related areas], Editio Cantor Aulendorf, 2001.

Tablets can be obtained, for example, by mixing the silibinin component with known excipients, for example inert diluents, such as calcium carbonate, calcium phosphate or lactose, disintegrants, such as corn starch or alginic acid, binders, such as starch or gelatin, lubricants, such as magnesium stearate or talc, and/or agents for achieving the depot effect, such as carboxymethylcellulose, cellulose acetate phthalate, or polyvinyl acetate. The tablets can also consist of a number of layers. Apart from the vehicles mentioned, the tablets can also contain additives, such as, for example, sodium citrate, calcium carbonate and dicalcium phosphate, together with various additional substances, such as starch, preferably potato starch, gelatin and the like. Furthermore, glidants, such as magnesium stearate, sodium lauryl sulfate and talc can additionally be used for tableting.

Sugar-coated tablets can be produced, for example, by coating cores produced analogously to the tablets with agents customarily used in sugar-coated tablet coatings, for example collidone or shellac, gum arabic, talc, titanium dioxide or sugar. For avoidance of a depot effect or for avoidance of incompatibilities, the core can also consist of a number of layers. The sugar-coated tablet coat can also consist of a number of layers for achieving a depot effect, it being possible to use the excipients mentioned above in the case of the tablets.

Juices, syrups, emulsions, suspensions and solutions for oral administration can additionally contain a sweetener, such as saccharin, cyclamate, glycerol or sugar, and a taste-enhancing agent, for example flavorings, such as vanillin or orange extract. They can moreover contain suspension auxiliaries or thickeners, such as sodium carboxymethylcellulose, wetting agents, for example condensation products of fatty alcohols with ethylene oxide, or preservatives, such as p-hydroxybenzoic acid esters.

Capsules can be produced, for example, by mixing the silibinin component with inert carriers, such as lactose or sorbitol, and encapsulating in gelatin capsules. Excipients which may be mentioned are, for example, water, pharmaceutically acceptable organic solvents, such as paraffins (e.g. petroleum fractions), oils of plant origin (e.g. peanut or sesame oil), mono- or polyfunctional alcohols (e.g. ethanol or glycerol), vehicles such as, for example, ground natural minerals (e.g. kaolins, clays, talc, chalk), ground synthetic minerals (e.g. highly disperse silicic acid and silicates), sugars (e.g. sucrose, lactose and dextrose), emulsifiers (e.g. lignin, sulfite waste liquors, methylcellulose, starch and polyvinylpyrrolidone) and glidants (e.g. magnesium stearate, talc, stearic acid and sodium lauryl sulfate).

The medicament can release the silibinin component immediately or in controlled form. If the release takes place in controlled form, the release preferably takes place in retarded form. Retarded release is understood according to the invention as preferably meaning a release profile in which the silibinin component is released over a relatively long period of time with a reduced rate of taking with the aim of a prolonged therapeutic action. This is achieved in particular in the case of oral administration. The expression "with at least partially retarded release" according to the invention comprises any medicament which guarantees a modified release of the silibinin component contained therein. The medicaments are preferably coated or uncoated administration forms which are produced using special excipients, according to particular processes or by combination of both possibilities, in order to selectively modify the release rate or the site of release. With respect to the time course of release, in the case of the medicaments according to the invention the following types are included: delayed release (extended release), repeat action release, prolonged release and sustained release. With respect to further details, reference can be made, for example, to K. H. Bauer et al., Lehrbuch der Pharmazeutischen Technologie [Textbook of Pharmaceutical Technology], 6th edition, WVG Stuttgart, 1999.

Suitable measures for the controlled release of active compound are known to the person skilled in the art. If the medicament is an oral administration form, for example a tablet, a delayed release can be achieved, for example, by embedding the silibinin component in a polymer matrix and/or film coating of the oral administration form with a membrane.

According to the invention, solid, semisolid or liquid medicaments with controlled release behavior can be employed. Solid medicaments are preferred, such as, for example, oral osmotic systems (OROS), coated tablets, matrix tablets, multilayer tablets, jacketed tablets, jacketed sugar-coated tablets, diffusion pellets, adsorbates and depot soft gelatin capsules. The oral medicament with controlled release of active compound is particularly preferably a coated tablet, jacketed tablet or matrix tablet, particularly preferably a matrix tablet.

The medicaments with controlled release of active compound can contain the silibinin component in dissolved, suspended and/or solid, amorphous or crystalline form.

For the production of the medicaments according to the invention with controlled release of active compound, the silibinin component can be employed in various particle sizes, e.g. in unground, ground or in micronized form.

In the medicaments with controlled release of active compound, the silibinin component is preferably present in the form of active substance-containing particles, such as, for example, pellets, granules, microcapsules, tablets, extrudates or crystals, which are coated with a diffusion-controlled membrane.

These diffusion-controlled medicaments are preferably multiparticulate, i.e. they preferably consist of a multiplicity of coated cores, such as, for example, of neutral pellets, to which a mixture of the silibinin component with a customary binder and thickener is applied, optionally together with customary excipients and vehicles, and are subsequently coated with a diffusion lacquer, the plasticizer and other excipients. The diffusion-controlled medicaments according to the invention can moreover consist of homogeneous cores comprising the silibinin component, which are produced, for example, by granulation, rotor granulation, fluidized bed agglomeration, tableting, moist extrusion or melt extrusion optionally with spheronization and are coated with a diffusion lacquer which can contain plasticizers and other excipients.

The particles which contain the silibinin component can contain excipients, such as, for example, acids or buffer substances, which modify the pH and thereby contribute in reducing the dependence of the release of the silibinin component on the pH of the release medium.

The diffusion-controlled membrane can moreover contain further excipients which owing to their pH-dependent solubility influence the permeability of the membrane at various pHs and thus contribute in minimizing the pH dependence of the release of the silibinin component.

The binders and thickeners used in the production of coated neutral pellets are preferably hydroxypropyl-methylcelluloses (HPMC) and polyvinylpyrrolidone (PVP). Likewise, other natural, synthetic or partially synthetic polymers such as, for example, methyl-cellulose (MC), hydroxypropylcellulose (HPC), other hydroxyalkylcelluloses and hydroxyalkylmethyl-celluloses, carboxymethylcelluloses and their salts, polyacrylic acids, polymethacrylates, gelatin, starch or starch derivatives can be employed.

For the production of pellets, particles and (mini)tablets which contain the silibinin component, cellulose, microcrystalline cellulose, cellulose derivatives, such as, for example, HMPC, HPC and low-substituted hydroxypropylcellulose (L-HPC), di-calcium phosphate, lactose, PVP and sucrose are preferably employed as binders and fillers by means of granulation, fluidized bed agglomeration, moist extrusion, tableting.

Melt extrusion pellets are produced by embedding the silibinin component in thermoplastic excipients. Suitable thermoplastic excipients are preferably HPC, HPMC, ethylcellulose, hydroxypropylmethylcellulose acetate succinate (HPMCAS), PVP, vinylpyrrolidone/vinyl acetate copolymer, polyethylene glycol, polyethylene oxide, polymethacrylates, polyvinyl alcohols (PVA), partially hydrolyzed polyvinyl acetate (PVA), polysaccharides, for example alginic acid, alginates, galactomannans, waxes, fats and fatty acid derivatives.

In the particles which contain the silibinin component, it is moreover possible to incorporate pH-modifying substances, such as, for example, acids, bases and buffer substances. By means of addition of these substances, it is possible to markedly reduce the pH dependence of the release of the silibinin component and its salts, hydrates, solvates.

The excipients employed which modify the pH in cores which contain the silibinin component are, for example, adipic acid, malic acid, L-arginine, ascorbic acid, aspartic acid, benzenesulfonic acid, benzoic acid, succinic acid, citric acid, ethanesulfonic acid, 2-hydroxyethanesulfonic acid, fumaric acid, gluconic acid, glucuronic acid, glutamic acid, potassium hydrogentartrate, maleic acid, malonic acid, methane-sulfonic acid, toluenesulfonic acid, trometamol, tartaric acid. Preferably, citric acid, succinic acid, tartaric acid and potassium hydrogentartrate are used.

For the production of the diffusion lacquer, ethyl-celluloses (e.g. Aquacoat® or Surelease®), and polymethacrylates (e.g. Eudragit® NE, Eudragit® RS and RL) are preferably suitable. However, other materials such as, for example, cellulose acetate and cellulose acetate butyrate can also be employed as film-forming diffusion-controlling polymers.

In addition to the diffusion-controlling polymer, the diffusion lacquer can also contain further excipients with pH-dependent solubility, such as, for example, enteric polymers such as cellulose phthalate, in particular cellulose acetate phthalate and hydroxy-propylmethyl-cellulose phthalate, cellulose succinates, in particular cellulose acetate succinate and hydroxy-propylmethylcellulose acetate succinate or polymethacrylates (e.g. Eudragit® L). By addition of these substances, it is possible to reduce the pH dependence of the release of the silibinin component.

Plasticizers used are, for example, citric acid derivatives, phthalic acid derivatives, benzoic acid and benzoic acid esters, other aromatic carboxylic acid esters, aliphatic dicarboxylic acid esters, glycerol mono-, glycerol di- or glycerol triacetate, polyols, fatty acids and their derivatives, acetylated fatty acid glycerides, castor oil and other native oils, miglyol and fatty acid alcohols.

In order to prevent sticking of the coated particles during the production and in the finished product, detackifiers, such as, for example, talc, magnesium stearate, glycerol monostearate and Aerosil, can be added to the lacquer.

The release rate is controlled by the lacquer composition and the thickness of the lacquer layer. Additives which increase the permeability of the film are pore-forming agents which can be added to the lacquer or to the particles to be coated which contain the silibinin component. Pore-forming agents employed are soluble polymers, such as, for example, polyethylene glycols, PVP, PVA, HPMC, HPC, hydroxyethylcelluloses (HEC), MC, carboxy-methylcelluloses or their salts, dextrins, maltodextrins, cyclodextrins, dextrans or other soluble substances, such as, for example, urea, sodium chloride, potassium chloride, ammonium chloride, sucrose, lactose, glucose, fructose, maltose, mannitol, sorbitol, xylitol and lactitol.

Excipients with pH-dependent solubility, which can be constituents of the diffusion film, are, for example, enteric polymers such as cellulose phthalates, in particular cellulose acetate phthalate and hydroxy-propylmethylcellulose phthalate, cellulose succinates, in particular cellulose acetate succinate and hydroxy-propylmethylcellulose acetate succinate and polymethacrylates (e.g. Eudragit® L).

In addition, the medicament with controlled release of the silibinin component can be a coated administration form which contains one or more swellable excipients which swell strongly on the penetration of liquid through the membrane and cause the coating to tear open as a result of the swelling and volume expansion. As a result of the tearing open of the coating, the release of pharmaceutical from the medicament is made possible (pulsatile release). As swellable excipients, these medicaments preferably contain polyvinyl-pyrrolidones, crospovidones, cross-linked sodium carboxymethylcellulose, cross-linked sodium carboxymethyl starch, polyethylene oxides, polymethacrylates, low-substituted hydroxypropylmethylcellulose (L-HPC). Suitable coating materials are preferably cellulose acetate, ethyl cellulose and polymethacrylates.

The coated, diffusion-controlled or pulsatile medicaments described can be employed directly and unchanged as a pharmaceutical form. They can, however, also be further processed, optionally with addition of excipients, to give the final administration form (e.g. capsule, tablet, sachet). In order to achieve a desired release profile, various coated particles can also be combined with one another in a pharmaceutical form, and an administration of an initial dose can take place, for example, by combination with rapidly releasing particles, e.g. uncoated pellets, granules or powders.

Medicaments with controlled release which can be used are also formulations which comprise the silibinin component in a matrix. These matrix formulations release the silibinin component by diffusion and/or erosion. Preferably, these medicaments are present in the form of a tablet or in the form of a number of tablets which, for example, can be encapsulated. The tablets can be coated or lacquered. Such medicaments are produced, for example, by mixing the constituents and direct tableting, or by dry or moist granulation with subsequent tableting.

The matrix-forming agents employed can be water-soluble, water-swellable or water-insoluble substances. Preferably, the medicaments contain one or more water-swellable polymers.

Water-soluble or water-swellable matrix-forming polymers employed are preferably hydroxy-propylmethyl-celluloses (HPMC), hydroxyethylmethylcelluloses, hydroxypropylcelluloses (HPC), hydroxyethylcelluloses, methylcelluloses (MC), ethylcelluloses, other alkyl-celluloses, hydroxyalkylcelluloses and hydroxyalkyl-methylcelluloses, sodium carboxymethylcelluloses (NaCMC), alginates, galactomannans, such as, for example, guar and carob bean flour, xanthans, polyethylene oxides, polyacrylic acids, polymethacrylic acids, polymethacrylic acid derivatives, polyvinyl alcohols (PVA), partially hydrolyzed polyvinyl acetate (PVAc), polyvinylpyrrolidone (PVP), agar, pectin, gum arabic, tragacanth, gelatin, starch or starch derivatives and mixtures of these substances. The use of HPMC is particularly preferred.

Furthermore, water-insoluble substances can be employed as structure-forming agents, for example unsaturated or saturated (hydrogenated) fatty acids and their salts, esters or amides, fatty acid mono-, di- or triglycerides, waxes, ceramides, cholesterol derivatives and mixtures of these substances.

The medicaments can furthermore contain customary tableting excipients, preferably highly disperse silica (Aerosil®), magnesium stearate, talc, PVP, lactose or microcrystalline cellulose.

Moreover, substances can be incorporated into the matrix which control the pH in the matrix. By the addition of such pH-modifying excipients and/or by the addition of substances which dissolve with increasing pH or dissolve out of the matrix and thus increase the porosity or permeability of the matrix and/or promote the erosion of the matrix, it is possible for these preferred embodiments of the present invention to achieve an almost pH-independent release.

The matrix which contains the silibinin component can also be present in special geometric forms in which the release is influenced by the special geometry and matrix surface. The matrix surface and release surface can be controlled, for example, by compression to give special formats (e.g. annular tablets), and/or by coating of subareas or application of barrier layers by means of a multilayer press.

Formulations with different release properties can preferably be combined to give a pharmaceutical form in multilayer or jacket-core tablets. For instance, by means of multilayer tablets which comprise a rapid-release layer, or jacket-core tablets having a rapidly releasing jacket the controlled releases according to the invention with high initial release of the silibinin component is achieved, while by means of jacket-core tablets with a rapid-release core an end-accelerated release can be achieved.

A further medicament with controlled release of the silibinin component is one wherein the silibinin component is embedded in a matrix consisting of one or more physiologically acceptable excipients by means of a melt process. The release of the silibinin component from these "melt extrudates" takes place by diffusion and/or erosion. Preferably, these formulations with controlled release of the silibinin component are present in the form of granules, pellets or tablets. The forms obtained by melt extrusion, in particular pellets and granules, can be processed to give other pharmaceutical forms, such as, for example, by encapsulation or tableting, optionally with addition of further pharmaceutically customary excipients. Moreover, the melt extrudates according to the invention can be ground and subsequently employed in this comminuted form for the production of other medicaments, such as, for example, matrix tablets. The further processing also comprises the combination of formulations having differing pharmaceutical release, such as, for example, retarded- and rapid-release particles, to give a medicament.

The melt extrudates and/or the pharmaceutical forms which are produced from melt extrudates can be coated or lacquered. The melt extrudates are preferably produced by mixing the silibinin component with at least one fusible physiologically acceptable excipient (carrier) and optionally further customary additional pharmaceutical substances, melting at a temperature in the range from 50 to 250° C., preferably 60 to 200° C., injection molding or extruding and shaping. In the course of this, the mixing of the components can take place either before the melting or during the melting, or some of the components are melted and the other constituents added to this melt. The mixture of the vehicle, the silibinin component and optionally present additional substances are thermoplastically deformable and can therefore be extruded. Numerous methods suggest themselves for the shaping of the mixture, for example hot granulation, cold granulation, calendering, extrusion and deformation of the still plastic strand or rounding.

Thermoplastic carriers used which are preferably swellable or soluble in physiological media are preferably: polyvinylpyrrolidone (PVP), copolymers of N-vinylpyrrolidone (NVP) and vinyl esters, in particular vinyl acetate, copolymers of vinyl acetate and crotonic acid, partially hydrolyzed polyvinyl acetate, polyvinyl alcohol, cellulose esters, cellulose ethers, in particular methylcellulose and ethyl-cellulose, hydroxyalkylcelluloses, in particular hydroxypropyl-cellulose, hydroxyalkylmethylcelluloses, in particular hydroxypropylmethylcellulose, and hydroxyethylmethylcellulose, carboxymethylcelluloses, cellulose phthalates, in particular cellulose acetate phthalate and hydroxypropylmethylcellulose phthalate, cellulose succinate, in particular cellulose acetate succinate and hydroxypropylmethylcellulose acetate succinate, polyhydroxyalkyl acrylates, polyhydroxyalkyl methacrylates, polyacrylates and polymethacrylates (Eudragit® types), copolymers of methyl methacrylate and acrylic acid, polylactides, polyethylene glycols, polyethylene oxides and polysaccharides such as galactomannans and alginic acid and its alkali metal and ammonium salts.

Preferred thermoplastic excipients for the production of the medicaments with controlled release of the silibinin component are HPC, PVP, vinylpyrrolidone/vinyl acetate copolymers, polymethacrylates, in particular Eudragit® L, HPMCAS, polyethylene glycols, polyethylene oxides and their mixtures. Plasticizing excipients which can be employed for the reduction of the glass transition temperature of the mixture are, for example, propylene glycol, glycerol, triethylene glycol, butanediols, pentanols, such as penta-erythritol, hexanols, long-chain alcohols, polyethylene glycols, polypropylene glycols, polyethylene/poly-propylene glycols, silicones, phthalic acid derivatives (e.g. dimethyl phthalate, diethyl phthalate, dibutyl phthalate), benzoic acid and benzoic acid esters, other aromatic carboxylic acid esters (e.g. trimellitic acid esters), citric acid derivatives (e.g. triethyl citrate, tributyl citrate, acetyltriethyl citrate), aliphatic dicarboxylic acid esters (e.g. dialkyl adipates, sebacic acid esters, in particular diethyl sebacate, tartaric acid esters), glycerol mono-, glycerol di- or glycerol triacetate, fatty acids and derivatives (e.g. glycerol monostearates, acetylated fatty acid glycerides, castor oil and other native oils, miglyol), fatty acid alcohols (e.g. cetyl alcohol, cetylstearyl alcohol), sugars, sugar alcohols and sugar derivatives (e.g. erythritol, isomalt, lactitol, mannitol, maltitol, maltodextrin, xylitol).

In addition to the silibinin component, carrier(s) and optionally plasticizer(s), the extrudable mixture can contain yet other pharmaceutically customary additional substances, for example lubricants and mold-release agents, glidants and flow agents, fillers and adsorbents, stabilizers, free radical traps, complexing agents, antioxidants, photostabilizers, propellants, surfactants, preservatives, colorants, sweeteners and flavorings.

Lubricants and mold-release agents can contain, for example, stearic acid and stearates, in particular aluminum, calcium and magnesium stearates, calcium behenate, sodium stearylfumarate, talc, silicones, waxes, and mono-, di- and triglycerides, such as, for example, glycerol monostearate, glycerol distearate, glycerol dibehenate, glycerol monooleate, glycerol palmitostearate.

Flow agents used are preferably animal and vegetable fats, preferably in hydrogenated form and with a melting point of at least 50° C., waxes (e.g. carnauba wax), mono-, di- and triglycerides (e.g. glycerol monostearate, glycerol distearates, glycerol di-behenate, glycerol monooleate, glyceryl palmito-stearate), phosphatides, in particular lecithin.

Fillers used are preferably substances such as titanium dioxide, aluminum oxide, magnesium oxide, silicic acid and silicates, stearic acid and stearates, cellulose derivatives (e.g. methylcellulose), starch and starch derivatives, sugars, sugar alcohols and sugar derivatives.

The medicaments with controlled release of the silibinin component can also be melt extrudates which contain excipients with pH-modifying properties and/or pH-dependent solubility. By means of these excipients (for example the acids, bases, buffer substances and enteric polymers already described beforehand), it is possible to minimize the pH dependence of the silibinin component release.

In the production of the melt extrudates the formation of "solid solutions" can occur, in which the silibinin component is present in the matrix in molecularly disperse form.

The medicaments with controlled release of the silibinin component can also be osmotic pharmaceutical release systems. In principle, osmotic systems of this type are known in the prior art. Here, the pharmaceutical release from the pharmaceutical form is in general based on an osmotic pressure as a driving force.

The osmotic system preferably consists of a core which contains the silibinin component, optionally a hydrophilic swelling agent and optionally a water-soluble substance for inducing the osmosis and optionally further pharmaceutically acceptable excipients, and a coat which consists of a water-permeable material which is impermeable for the components of the core and has at least one opening, through which constituents present in the core can be released.

The material from which the coat of these medicaments according to the invention with controlled release of the silibinin component is formed is semipermeable, i.e. permeable for water, aqueous media and biological fluids and not or very restrictedly permeable for the components of the core, and suitable for film formation. The selectively semipermeable encasing material is insoluble in body fluids, does not erode, is not degraded in the GI tract and is excreted unchanged, or it shows bioerosion only toward the end of the release period.

Typical materials for the production of the coats of the osmotic system are preferably acylated cellulose derivatives (cellulose esters), which are mono- to trisubstituted by acetyl groups or mono- to disubstituted by acetyl groups and a further acyl radical other than acetyl, for example cellulose acetate, cellulose triacetate, cellulose acetate/ethyl carbamate, cellulose acetate phthalate, cellulose acetate methylcarbamate, cellulose acetate succinate, cellulose acetate dimethylamino acetate, cellulose acetate diethylamino acetate, cellulose acetate ethyl-carbonate, cellulose acetate chloroacetate, cellulose acetate ethyloxalate, cellulose acetate methylsulfonate, cellulose acetate butylsulfonate, cellulose acetate propionate, cellulose acetate octate, cellulose acetate laurate, cellulose acetate p-toluene sulfonate, cellulose acetate butyrate and other cellulose acetate derivatives and also agar acetate and amylose acetate.

A suitable semipermeable membrane material of the osmotic system is furthermore ethylcellulose, copolymers of alkylene oxide and alkyl glycidyl ether, polymeric epoxides, polyglycols and polylactic acid derivatives. Moreover, mixtures of water-insoluble acrylates per se, for example a copolymer of ethyl acrylate and methyl methacrylate, can be employed.

If necessary, the coat of the osmotic system can also contain plasticizers, such as, for example, the plasticizing substances already mentioned beforehand, and other additional substances, such as, for example, pore-forming agents. If required, a photoprotective lacquer can be applied to the semipermeable coat, which can consist, for example, of HPMC or HPC, and a suitable plasticizer (e.g. polyethylene glycol) and pigments (e.g. titanium dioxide, iron oxides).

In order to be able to administer an initial dose of the silibinin component, the osmotic system can also be provided with a coat which contains the silibinin component, from which the silibinin component is preferably rapidly released on contact with the release medium before the osmotically controlled release of the silibinin component from the core begins.

Suitable water-swellable polymers which can be present in the core of the osmotic system are preferably polyethylene oxides (e.g. Polyox®), xanthan gum, copolymers of vinylpyrrolidone and vinyl acetate, polyvinylpyrrolidones, crospovidones, cross-linked sodium carboxymethylcellulose, cross-linked sodium carboxymethyl starch, low-substituted hydroxypropyl-methylcellulose (L-HPC), poly(hydroxyalkyl meth-acrylate), alginates and galactomannans and also further hydrophilic polymeric swelling agents and mixtures thereof.

Suitable osmotically active substances which can be added to the core for the induction of osmosis are water-soluble salts of inorganic and organic acids or nonionic organic substances with high water solubility, such as, for example, carbohydrates, in particular sugars, or amino acids. By way of example, a few substances may be mentioned which can be incorporated into the core of the osmotic system individually or as a mixture for the induction of osmosis: inorganic salts such as chlorides, sulfates, sulfites, carbonates, bicarbonates, phosphates, hydrogenphosphates and dihydrogenphosphates of the alkali metals and alkaline earth metals, such as, for example, sodium, lithium, potassium, calcium or magnesium, organic acids such as adipic acid, ascorbic acid, succinic acid, citric acid, fumaric acid, maleic acid, tartaric acid, benzoic acid and their alkali metal or alkaline earth metals salts, acetates, pentoses, such as, for example, arabinose, ribose or xylose, hexoses, such as, for example, glucose, fructose, galactose or mannose, disaccharides, such as, for example, sucrose, maltose or lactose, trisaccharides, such as, for example, raffinose, sugar alcohols, such as, for example, mannitol, sorbitol, maltitol, xylitol or inositol, and urea. Sodium chloride and sodium carbonate are particularly preferably used.

Moreover, the osmotic system can contain other pharmaceutically customary additional substances, such as, for example, lubricants and mold-release agents, glidants, binders, color pigments, thickeners, protective colloids, stabilizers and surfactants.

The production of the osmotic release system is preferably carried out with the aid of standard techniques, such as, for example, moist granulation or dry compaction, tableting and subsequent organic coating.

The coat of the osmotic system has at least one outlet opening, through which the silibinin component, optionally together with other constituents of the core, is released. The opening can be introduced into the coats in various ways, for example by punching, mechanical drilling or by means of a laser drill. The term "opening" also comprises bioerodible materials, which dissolve out of the coat on administration of this medicament according to the invention and thus lead to the formation of outlet openings in situ.

In a further embodiment for the controlled release of the silibinin component, the silibinin component can also be present as an ion exchange complex (adsorbate).

Preferably, the medicament is formulated for once daily (q.d.), twice-daily (b.i.d.), three times daily (t.i.d.) or four-times daily administration.

In a preferred embodiment, 0.5 to 75% by weight of the originally contained silibinin component have been released from the medicament after 1 h under in vitro conditions. Suitable conditions for the determination of the in vitro release of active substances are known to the person skilled in the art. In this connection, reference can be made, for example, to the European Pharmacopeia. Preferably, the determination of the release is carried out with the aid of a blade stirrer apparatus in artificial gastric juice (buffer pH 1.2) or artificial intestinal juice (buffer pH 7.6). The amount of the silibinin component released can be analyzed, for example, with the aid of HPLC and UV detection.

Preferred release profiles $A_1$ to $A_8$ are summarized in the following table:

| after [h] | $A_1$ % by wt. | $A_2$ % by wt. | $A_3$ % by wt. | $A_4$ % by wt. | $A_5$ % by wt. | $A_6$ % by wt. | $A_7$ % by wt. | $A_8$ % by wt. |
|---|---|---|---|---|---|---|---|---|
| 0.5 | 5.0-34 | 6.0-33 | 7.0-32 | 9.0-31 | 11-30 | 13-30 | 15-29 | 17-28 |
| 1 | 12-53 | 15-52 | 18-50 | 20-48 | 22-46 | 24-44 | 27-42 | 30-40 |
| 2 | 25-74 | 27-71 | 29-68 | 31-65 | 33-62 | 36-60 | 39-58 | 42-56 |
| 3 | 33-85 | 36-82 | 39-79 | 42-76 | 45-73 | 48-71 | 50-69 | 52-67 |
| 4 | 41-92 | 44-89 | 47-86 | 50-83 | 53-81 | 55-79 | 58-77 | 60-75 |
| 6 | 52-98 | 55-97 | 58-96 | 60-94 | 63-92 | 66-90 | 69-88 | 72-86 |
| 8 | >62 | >65 | >68 | 71-99 | 74-98 | 76-98 | 78-97 | 80-97 |
| 12 | >70 | >73 | >76 | >79 | >82 | >84 | >86 | >88 |

In a preferred embodiment, the medicament contains a cyclodextrin and/or a phospholipid.

Pharmaceutical formulations which contain silibinin and cyclodextrins are known in the prior art (cf., for example, EP 422 497). Preferably, the silibinin forms an inclusion complex with the cyclodextrin. Preferred cyclodextrins are α-, β- and γ-cyclodextrins, their O—$C_1$-$C_4$-alkyl and hydroxy-$C_1$-$C_4$-alkyl derivatives.

Pharmaceutical formulations which contain silibinin and phospholipids are likewise known in the prior art (cf. U.S. Pat. No. 4,764,508). Preferably, the silibinin forms a complex with the phospho-lipid. Preferred phospholipids are phosphatidylcholine, phosphatidylethanolamine and phosphatidylserine. Preferred silibinin phospholipid complexes are ternary complexes additionally containing vitamin E (α-tocopherol). Complexes of this type are known from the prior art as "SPV complexes" (cf. A Federico, Gut. 2006, 55(6), 901-2).

In addition to the silibinin component, the medicament can contain one or more terpenes. By means of the action of the terpene, both the absorption requirements and the absorption processes and thus the absorption can be improved overall. The terpenes can be natural or synthetic ethereal oils and/or their terpenoid constituents in the form of the pure substances or mixtures or derivatives of these pure substances. Among the ethereal oils, mention may be made in particular of thyme oil, eucalyptus oil, pine needle oil, tea tree oil, cajeput oil, cardamon oil, peppermint oil, sage oil and rosemary oil, preferably thyme oil. For the terpenes as substances which are also intended to include terpenoid substances, mention may be made in particular of the hemiterpenes such as, for example, isoprene, tiglic acid, angelic acid, isovaleric acid; the monoterpenes, including the acyclic monoterpenes such as, for example, 2,6-dimethyloctane, α-myrcene, (E)-p-ocimene, perillene, linalool, geranial, (S)-(+)citronellal and the monocyclic monoterpenes such as, for example, cyclopropane monoterpenes and cyclobutane monoterpenes such as chrysanthemic acid or junionone, cyclopentane monoterpenes such as, for example, iridoids or nepetalactones or (−)-secologanin and (−)-oleuropein, cyclohexane monoterpenes such as o-menthane, cis- or trans-p-menthane, (R)-(+)-limonene, terpinols, (−)-menthol, (+)-perillaaldehyde, (−)-menthone or (+)-carvone, bicyclic monoterpenes such as the oxygen-bridged terpenes 1,4-cineol, 1,8-cineol, or ascaridol; the cyclopropane bicycles carane and thujane, the cyclobutane bicycle pinane, and the bicycloheptanes camphane and fenchane; the sesqui-terpenes such as farnesane, bisabolane, germacrane elemane, and humulane. Particularly preferred terpenes are thymol, menthol, cineol, borneol, carvone, limenone and pinene, usually preferably thymol.

The medicament contains a silibinin component. Silibinin is a constituent of silymarin. Preferably, in addition to silibinin or the silibinin components, the medicament contains none of the other constituents of silymarin. If the silibinin component is silibinin as such, the medicament preferably contains none of the other constituents of silymarin. If the silibinin component is not silibinin as such, but, for example, a silibinin ester, the medicament preferably contains no constituents of silymarin at all, i.e. also no silibinin.

Preferably, one or more of the substances selected from the group consisting of isosilibinin, silidianin, silichristin, taxifolin, isosilichristin, silimonin, silandrin, silihermin and neosilihermin is not contained in the medicament, i.e. the medicament is preferably essentially free of at least one of the above mentioned substances. In this connection, "essentially free" means that the residual contents of the substance concerned is preferably less than 2.0% by weight, more preferably less than 1.0% by weight, even more preferably less than 0.5% by weight, most preferably less than 0.1% by weight and in particular less than 0.05% by weight, based on the total weight of the medicament. Analytical methods for the determination of the residual content of these substances are known to the person skilled in the art, for example HPLC.

It has been found that the individual constituents of silymarin differ in their chemical and physical properties and contribute to the pharmacological activity of silymarin to a very different extent such that it is advantageous to administer silibinin or its derivatives and/or salts as the only constituent of silymarin, i.e. uniquely. It appears that in this way both the efficacy and the patient compliance can be improved.

Furthermore, it has been surprisingly found that the tolerability of the various constituents of silymarin differs from one another and that silibin is more tolerable, particularly less toxic, than silymarin (i.e. than the mixture containing other compounds besides silibinin).

In a preferred embodiment, the invention relates to the use of a silibinin component for the production of a medicament which is preferably formulated for parenteral or oral administration and beside the silibinin component contains none of the other constituents of silymarin, for the treatment of viral hepatitis, in particular of hepatitis B or C.

Particularly preferred medicaments that are adapted for oral administration of the silibinin component are described here below. All these oral dosage forms have in common that they preferably contain the silibinin component in substantially pure form, i.e., preferably in the absence of other constituents of silymarin, particularly in the absence of isosilibinin and/or silichristin and/or silidianin.

Preferably, the oral dosage forms are immediate release dosage forms, i.e. the silibinin component is rapidly released therefrom thereby leading to a rapid onset of the drug in the gastrointestinal tract. In a preferred embodiment, 30 minutes after administration of the oral dosage form, at least 75 wt.-%, more preferably at least 80 wt.-%, still more preferably at least 85 wt.-%, most preferably at least 90 wt.-% and in particular at least 95 wt.-% of the originally contained silibinin component have been released from the oral dosage form.

In a preferred embodiment, the medicament is provided as a solid solution. The solid solution is preferably realized by embedding the silibinin component in molecular disperse form in a highly soluble, preferably amorphous polymer matrix having a large specific surface area. The silibinin component should be present in molecular disperse form, i.e., neither micro-crystalline nor fine crystalline. A highly soluble, amorphous state may already be achieved by utilizing highly soluble, solid polymeric solvents when extracting silibinin or the silibinin component from the silymarin extract. This technical drug formulation increases the solubility of the silibinin component and its dissolution rate.

An example of such a solid solution comprises the silibinin component, a suitable polymer (e.g. a polyvinylpyrrolidone (PVP) or a polyvinylpyrrolidone copolymer, such as Kollidon® 25), and optionally, a dextrin (e.g. maltodextrin). The formulation may contain further excipients, such as aerosil and/or talkum.

Preferred embodiments $B_1$ to $B_6$ of the solid solution are displayed in the table here below:

| wt.-% | $B_1$ | $B_2$ | $B_3$ | $B_4$ | $B_5$ | $B_6$ |
|---|---|---|---|---|---|---|
| silibinin component | 1.0-50 | 2.5-20 | 8.0 ± 5.0 | 8.0 ± 4.0 | 8.0 ± 3.0 | 8.0 ± 2.0 |
| PVP | 1.0-97 | 10-80 | 64 ± 15 | 64 ± 12 | 64 ± 10 | 64 ± 7.0 |
| dextrin | 1.0-70 | 5.0-50 | 22.8 ± 20 | 22.8 ± 15 | 22.8 ± 10 | 22.8 ± 7.0 |
| aerosil | 0-10 | 0-7.5 | 4.0 ± 3.0 | 4.0 ± 2.5 | 4.0 ± 2.0 | 4.0 ± 1.5 |
| talkum | 0-5.0 | 0-2.5 | 1.2 ± 1.0 | 1.2 ± 0.7 | 1.2 ± 0.5 | 1.2 ± 0.3 |

The formulation may be provided, e.g., in a hard gelatine capsule.

In another preferred embodiment, the medicament is provided as a self-emulsifying microemulsion. Self-emulsifying lipid-systems can be used as carriers and can lead to a high bioavailability of the drug contained therein. The lipid-system is of colloidal nature and this allows for resorption of microparticles, especially of colloidal size, also via the lymphatic system in the gastrointestinal tract. Typically, the dissolved drug is saturated but re-crystallization does not occur. Upon per oral administration of lipophilic drugs, e.g. of the silibinin component, the microemulsion primarily serves as an optimized vehicle that enhances the dissolution rate of the dissolved or highly disperse drug at the location of absorption. In other words, the lipid system acts as absorption enhancer.

An example of such a lipid-system comprises the silibinin component, a suitable first emulsifier (e.g. lauroyl macrogolglyceride, such as Gelucire® 44/14), and optionally, a suitable second emulsifier (e.g. caprylocapryl macrogolglyceride, such as Labrasol®). The formulation may contain further excipients, such as polysorbat.

Preferred embodiments $C_1$ to $C_6$ of the solid solution are displayed in the table here below:

| wt.-% | $C_1$ | $C_2$ | $C_3$ | $C_4$ | $C_5$ | $C_6$ |
|---|---|---|---|---|---|---|
| silibinin component | 0.1-50 | 0.5-20 | 4.0 ± 3.5 | 4.0 ± 3.0 | 4.0 ± 2.5 | 4.0 ± 2.0 |
| first emulsifier | 1.0-99 | 5-97 | 54 ± 15 | 54 ± 12 | 54 ± 10 | 54 ± 7.0 |
| second emulsifier | 0-70 | 0-70 | 41 ± 20 | 41 ± 15 | 41 ± 10 | 41 ± 7.0 |
| polysorbat | 0-10 | 0-7.5 | 1.5 ± 1.0 | 1.5 ± 0.7 | 1.5 ± 0.5 | 1.5 ± 0.3 |

The formulation, which may be solid or preferably, semi-liquid, may be provided, e.g., in a hard gelatine capsule or as a soft gelatine capsule.

In still another preferred embodiment, the medicament is provided as a nanotechnological formulation. The average particle size of the nanoparticles is preferably below 1 µm. Nanoparticles are capable of passing biological membranes of cell structures. The silibinin component is preferably adsorbed to the surface of said nanopaticles. The nanoparticles are preferably selected from the group consisting of inorganic nanoparticles and organic nanoparticles.

Inorganic nanoparticles comprise crystalline silicates from e.g. mineral origin or artificial silicates, such as metallosilicates, for example alumosilicates (e.g. zeolites). These inorganic nanoparticles are preferably chemically modified so that they bear electrostatic charges. The silicates are ultra finely ground to nanoparticles and the silibinin component is bound (adsorbed) to the microporous surface of the nanoparticles.

Organic nanoparticles include clusters or agglomerates of small proteins or oligopeptides or of lipids. A suitable protein carrier is for example protamin.

Methods for the preparation of nanoparticles are known to the skilled artisan. For example, colloidal nanoparticles as carriers for per oral drug release can be prepared by spraying the drug, i.e., the silibinin component, together with suitable carrier materials under pressure at, e.g., 60° C. through jets being equipped with perforated strainers (matrices) into strongly cooled towers. Spontaneous cooling forms an amorphous phase consisting of nanoparticles.

Solid lipid nanoparticles, for examples, can be prepared by this high-pressure-homogenization and subsequent spray-cooling. Preferably, the drug, i.e. the silibinin component, is employed as a solution in a suitable solvent or inform of sub-microparticles. The silibinin component can be sprayed and pressure-homogenized, respectively, in admixture with a lipid vehicle and a surfactant at, e.g., 60° C. After the optional addition of fine filler materials as outer phase as well as glidants and further surfactants, the thus obtained formulation can be filled into hard gelatine capsules.

An example of such solid lipid nanoparticles comprises a core of the silibinin component, a suitable first emulsifier (e.g. stearoyl macrogolglyceride, such as Gelucire® 50/13), and optionally, a suitable macromolecular nonionic surfactant (e.g. poloxamer). The formulation preferably further contains an outer phase (coating) comprising a first surfactant (e.g. Tween 20), aerosil and a second surfactant (e.g. glyceryl palimitostearate, such as Percirol®).

Preferred embodiments $D_1$ to $D_6$ of the solid solution are displayed in the table here below:

| wt.-% | $D_1$ | $D_2$ | $D_3$ | $D_4$ | $D_5$ | $D_6$ |
|---|---|---|---|---|---|---|
| silibinin component | 0.1-30 | 0.5-20 | 4.5 ± 3.0 | 4.5 ± 2.5 | 4.5 ± 2.0 | 4.5 ± 1.5 |
| first emulsifier | 10-99 | 20-95 | 75 ± 20 | 75 ± 15 | 75 ± 10 | 75 ± 7.5 |
| macromolecular nonionic surfactant | 0-50 | 0-40 | 15 ± 10 | 15 ± 7.5 | 15 ± 5 | 15 ± 2.5 |
| first surfactant | 0-10 | 0.1-7.5 | 1.5 ± 0.7 | 1.5 ± 0.5 | 1.5 ± 0.3 | 1.5 ± 0.2 |
| aerosil | 0-10 | 0.1-7.5 | 3.0 ± 2.0 | 3.0 ± 1.5 | 3.0 ± 1.0 | 3.0 ± 0.7 |
| second surfactant | 0-10 | 0.1-7.5 | 1.5 ± 0.7 | 1.5 ± 0.5 | 1.5 ± 0.3 | 1.5 ± 0.2 |

The loaded nanoparticles achieve a substantially quicker onset of the drug.

The medicament contains the silibinin component preferably in a dose of at least 10 mg, at least 15 mg, at least 20 mg, at least 25 mg, at least 50 mg, at least 75 mg, at least 100 mg, at least 125 mg, at least 150 mg, at least 175 mg or at least 200 mg; more preferably at least 225 mg, at least 250 mg, at least 275 mg, at least 300 mg, at least 325 mg, at least 350 mg, at least 375 mg or at least 400 mg; even more preferably at least 425 mg, at least 450 mg, at least 475 mg, at least 500 mg, at least 525 mg, at least 550 mg, at least 575 mg or at least 600 mg; most preferably at least 625 mg, at least 650 mg, at least 675 mg, at least 700 mg, at least 725 mg, at least 750 mg, at least 775 mg or at least 800 mg; and in particular at least 825 mg, at least 850 mg, at least 875 mg, at least 900 mg, at least 925 mg, at least 950 mg, at least 975 mg, or at least 1000 mg; in each case as an equivalent dose based on silibinin.

The medicament contains the silibinin component preferably in a dose of at least 1.0 mg/kg, more preferably at least 2.5 mg/kg, even more preferably at least 5.0 mg/kg, most preferably at least 7.5 mg/kg and in particular at least 10 mg/kg, at least 12.5 mg/kg, at least 15 mg/kg, at least 17.5 mg/kg, at least 20 mg/kg, at least 22.5 mg/kg, at least 25 mg/kg, at least 27.5 mg/kg or at least 30 mg/kg, based on the bodyweight of the patient and in each case as an equivalent dose based on silibinin. Preferably, said dose is a daily dose. Thus, when the medicament is adapted for, e.g., administration twice daily, the respective daily dose is divided into two portions of identical amount. Analogously, when the medicament is adapted for, e.g., administration thrice daily, the respective daily dose is divided into three portions of identical amount.

In a preferred embodiment, the daily dose of the silibinin component is at least 5, more preferably at least 10, still more preferably at least 15 and most preferably at least 20 mg per kg body weight, based on the equivalent weight of silibinin.

In a preferred embodiment, the daily dose of the silibinin component is 20 mg per kg body weight, based on the equivalent weight of silibinin. Thus, when the medicament is adapted for administration once daily, it preferably contains the entire amount of the silibinin-component, e.g. 1400 mg silibinin for a patient having a body weight of 70 kg. When the medicament is adapted for administration twice daily, it preferably contains half the amount of the silibinin-component, e.g., 700 mg silibinin for a patient having a body weight of 70 kg. When the medicament is adapted for administration thrice daily, it preferably contains a third of the amount of the silibinin-component, e.g., 467 mg silibinin for a patient having a body weight of 70 kg. When the medicament is adapted for administration four times daily, it preferably contains a quart of the amount of the silibinin-component, e.g., 350 mg silibinin for a patient having a body weight of 70 kg.

1200 mg or at least 1250 mg; and in particular at least 1300 mg, at least 1350 mg, at least 1400 mg, at least 1450 mg or at least 1500 mg; in each case as an equivalent dose based on silibinin.

Preferred pharmacokinetic parameters $AUC_{0-t}$, $AUC_{t-\infty}$, $AUC_{0-\infty}$ and $AUC_{0-\infty}$ (corr.) (preferably after several infusions, e.g. after 11 infusions; single dose: 12.5 mg/kg; daily dose: 4 infusions; total dose: 11 infusions) are summarized as embodiments $E_1$ to $E_8$ in the following table:

|  | $E_1$ µg h/ml | $E_2$ µg h/ml | $E_3$ µg h/ml | $E_4$ µg h/ml | $E_5$ µg h/ml | $E_6$ µg h/ml | $E_7$ µg h/ml | $E_8$ µg h/ml |
|---|---|---|---|---|---|---|---|---|
| $AUC_{0-t}$ | 333 ± 200 | 333 ± 150 | 333 ± 125 | 333 ± 100 | 333 ± 80 | 333 ± 60 | 333 ± 40 | 333 ± 20 |
| $AUC_{t-\infty}$ | 322 ± 200 | 322 ± 150 | 322 ± 125 | 322 ± 100 | 322 ± 80 | 322 ± 60 | 322 ± 40 | 322 ± 20 |
| $AUC_{0-\infty}$ | 655 ± 200 | 655 ± 150 | 655 ± 125 | 655 ± 100 | 655 ± 80 | 655 ± 60 | 655 ± 40 | 655 ± 20 |
| $AUC_{0-\infty}$(corr.) | 414 ± 200 | 414 ± 150 | 414 ± 125 | 414 ± 100 | 414 ± 80 | 414 ± 60 | 414 ± 40 | 414 ± 20 |

When the medicament is adapted for parenteral administration, preferably for infusion, a preferred treating regimen comprises 4 identical infusions lasting 2 hours each. Preferably, after 4 hours the same infusion is repeated so that per 24 hours 4 infusions are administered in total. Such a regimen can be schematically abbreviated as "2-4-2-4-2-4-2-4", where each figure denotes a number of hours and the underlined figures denote the duration of an infusion whereas the non-underlined figures denote a lag phase in between two infusion intervals. Preferably, the treating regimen is even, i.e. per 24 hours all infusions are identically dosed over identical periods of time and the lag phases between consecutive infusions are identical as well.

Following the above denotation, preferred parenteral administration regimens are summarized in the table here below:

| once daily | 0.5-23.5; 1-23; 1.5-22.5; 2-22; 2.5-21.5; 3-21; 3.5-20.5; 4-20; 6-18; 12-12; 24; |
|---|---|
| twice daily | 0.5-11.5-0.5-11.5; 1-11-1-11; 1.5-10.5-1.5-10.5; 2-10-2-10; 2.5-9.5-2.5-9.5; 3-9-3-9; 3.5-8.5-3.5-8.5; 4-8-4-8; 6-6-6-6; 8-4-8-4; |
| three times daily | 0.5-7.5-0.5-7.5-0.5-7.5; 1-7-1-7-1-7; 1.5-6.5-1.5-6.5-1.5-6.5; 2-6-2-6-2-6; 2.5-5.5-2.5-5.5-2.5-5.5; 3-5-3-5-3-5; 3.5-4.5-3.5-4.5-3.5-4.5; 4-4-4-4-4-4; 6-2-6-2-6-2; |
| four times daily | 0.5-5.5-0.5-5.5-0.5-5.5-0.5-5.5; 1-5-1-5-1-5-1-5; 1.5-4.5-1.5-4.5-1.5-4.5-1.5-4.5; 2-4-2-4-2-4-2-4; 2.5-3.5-2.5-3.5-2.5-3.5-2.5-3.5; 3-3-3-3-3-3-3-3; 3.5-2.5-3.5-2.5-3.5-2.5-3.5-2.5; and 4-2-4-2-4-2-4-2. |

In a preferred embodiment, the medicament is adapted for administration once, twice, thrice or four times daily so that the overall daily dose that is administered when administering the medicament in the prescribed mode, amounts to at least 300 mg, at least 325 mg, at least 350 mg, at least 375 mg or at least 400 mg; more preferably at least 425 mg, at least 450 mg, at least 475 mg, at least 500 mg, at least 525 mg, at least 550 mg, at least 575 mg or at least 600 mg; still more preferably at least 625 mg, at least 650 mg, at least 675 mg, at least 700 mg, at least 725 mg, at least 750 mg, at least 775 mg or at least 800 mg; yet more preferably at least 825 mg, at least 850 mg, at least 875 mg, at least 900 mg, at least 925 mg, at least 950 mg, at least 975 mg, or at least 1000 mg; most preferably at least 1050 mg, at least 1100 mg, at least 1150 mg, at least In a preferred embodiment of the invention, the medicament containing the silibinin component is adapted for adjunct therapy, preferably to immuno-modulatory/antiviral combination therapies such as interferon/ribovarin.

In a preferred embodiment, in addition to the silibinin component the medicament contains a further pharmaceutical, which preferably is suitable for the treatment of inflammatory liver diseases, particularly preferably of viral liver diseases, in particular for the treatment of hepatitis B or C.

Preferably, the further pharmaceutical is selected from the group consisting of liver therapeutics, lipotropics [A05B]; nucleosides, nucleotides, exclusive inhibitors of reverse transcriptase [J05AB]; interferons [L03AB] and monoclonal antibodies to HBV (hepatitis B virus). The notations indicated in square brackets relate to the ATC index, preferably in the German version of 2007.

Particularly preferably, the further pharmaceutical is selected from the group consisting of arginine glutamate, citiolone, epomediol, ornithine oxoglurate, tidiacicarginine, myoinositol, methionine and N-acetyl-methionine, choline, ornithine aspartate, cianidanol, tiopronine, betaine, cyanocobalamin, leucine, laevulose, aciclovir, idoxuridine, vidarabine, ribavirin, ganciclovir, famciclovir, valaciclovir, cidofovir, penciclovir, valganciclovir, brivudine, interferon alfa, interferon beta, interferon gamma, interferon alfa-2a, interferon alfa-2b, interferon alfa-n1, interferon beta-1a, interferon beta-1b, interferon alfacon-1, peginterferon alfa-2b, peginterferon alfa-2a and interferon gamma 1b.

In a preferred embodiment, the treatment of the patient with the silibinin component serves for the support and/or preparation of a treatment of viral hepatitis, in particular of hepatitis B or C, following this treatment, with another pharmaceutical which is preferably selected from the group consisting of arginine glutamate, silymarin, citiolone, epomediol, ornithine oxoglurate, tidiacicarginine, myoinositol, methionine and N-acetyl-methionine, choline, ornithine aspartate, cianidanol, tiopronine, betaine, cyanobalamin, leucine, laevulose, aciclovir, idoxuridine, vidarabine, ribavirin, ganciclovir, famciclovir, valaciclovir, cidofovir, penciclovir, valganciclovir, brivudine, interferon alfa, interferon beta, interferon gamma, interferon alfa-2a, interferon alfa-2b, interferon alfa-n1, interferon beta-1a, interferon beta-1b, interferon alfacon-1, peginterferon alfa-2b, peginterferon alfa-2a and interferon gamma 1b.

Thus, preferably following the treatment of viral hepatitis, in particular of hepatitis B or C, with the medicament which contains the silibinin component, the treatment of the viral hepatitis, in particular of hepatitis B or C, with another medicament takes place.

In a preferred embodiment, the medicament is formulated as a constituent of a sequential treatment, the medicament initially being administered for a first period, preferably parenterally, and subsequently another medicament being administered for a second period. Preferably, the first period comprises at least 2 days, more preferably at least 3 days, even more preferably at least 4 days, most preferably at least 5 days and in particular at least 6 days. Preferably, the second period comprises more days than the first period. Preferably, the second period comprises at least two days, more preferably at least 3 days, even more preferably at least 4 days, most preferably at least 5 days and in particular at least 6 days. In a particular preferred embodiment, the second medicament contains a combination of ribavirin and pegylated interferon alfa and the second period comprises a time of 24 to 48 weeks.

Preferably, the other medicament contains one or more pharmaceuticals selected from the group consisting of arginine glutamate, silymarin, citiolone, epomediol, ornithine oxoglurate, tidiacicarginine, myoinositol, methionine and N-acetylmethionine, choline, ornithine aspartate, cianidanol, tiopronine, betaine, cyanocobalamin, leucine, laevulose, aciclovir, idoxuridine, vidarabine, ribavirin, ganciclovir, famciclovir, valaciclovir, cidofovir, penciclovir, valganciclovir, brivudine, interferon alfa, interferon beta, interferon gamma, interferon alfa-2a, interferon alfa-2b, interferon alfa-n1, interferon beta-1a, interferon beta-1b, interferon alfacon-1, peginterferon alfa-2b, peginterferon alfa-2a, interferon gamma 1b and monoclonal antibodies to HBV, particularly preferably an interferon and/or ribavirin and/or silymarin. If the other medicament contains an interferon, this is preferably pegylated interferon alfa (peginterferon alfa-2a or peginterferon alfa-2b).

In a particularly preferred embodiment, the other medicament contains one or more pharmaceuticals selected from the group consisting of isosilibinin, silidianin, silichristin, taxifolin, isosilichristin, silimonin, silandrin, silihermin and neosilihermin, more preferably only one pharmaceutical selected from the foregoing list. Preferably, the other medicament contains a silibinin-component as defined in connection with the medicament described above which is administered for the first period, and is preferably essentially free of at least one, preferably all, of the abovementioned substances. In this connection, "essentially free" means that the residual contents of the substance concerned is preferably less than 2.0% by weight, more preferably less than 1.0% by weight, even more preferably less than 0.5% by weight, most preferably less than 0.1% by weight and in particular less than 0.05% by weight, based on the total weight of the medicament.

The other medicament can in principle be formulated for parenteral or oral administration. According to the invention, it is preferably formulated for another administration route than the medicament which is administered for the first period. Particularly preferably, the other medicament is formulated for oral administration. In a particularly preferred embodiment according to the invention, the medicament that is administered during the first period is adapted for parenteral, preferably intravenous administration, and the other medicament that is administered during the second period which follows the first period is adapted for oral administration.

In a preferred embodiment, the treating regimen according to the invention comprises two phases which follow one another consecutively, namely a first period and a second period. Preferably, during the first period the medicament containing the silibinin component is administered, preferably parenterally, but no other medicament having a hepatic effect is administered simultaneously. During the second period another medicament is administered which preferably contains ribavirin and/or pegylated interferon alfa. In a preferred embodiment, the medicament containing the silibinin component is also administered during the second period, preferably parenterally. In another preferred embodiment, the medicament containing the silibinin component is not administered during the second period, i.e., only said other medicament is administered.

Preferred embodiments $F_1$ to $F_{15}$ of the biphasic treating regimen are summarized in the table here below:

| no. of days | $F_1$ | $F_2$ | $F_3$ | $F_4$ | $F_5$ | $F_6$ | $F_7$ | $F_8$ | $F_9$ | $F_{10}$ | $F_{11}$ | $F_{12}$ | $F_{13}$ | $F_{14}$ | $F_{15}$ |
|---|---|---|---|---|---|---|---|---|---|---|---|---|---|---|---|
| first period | ≥1 | ≥1 | ≥2 | ≥2 | ≥2 | ≥3 | ≥3 | ≥4 | ≥3 | ≥4 | ≥4 | ≥5 | ≥5 | ≥7 | ≥7 |
| second period | ≥1 | ≥2 | ≥1 | ≥2 | ≥3 | ≥2 | ≥3 | ≥3 | ≥4 | ≥4 | ≥5 | ≥4 | ≥5 | ≥7 | ≥14 |

In another preferred embodiment, the treating regimen according to the invention comprises three phases which follow one another consecutively, namely a first period, a second period and a third period. Preferably, during the first period the medicament containing the silibinin component is administered, preferably parenterally, but no other medicament having a hepatic effect is administered simultaneously. During the second period another medicament which preferably contains ribavirin and/or pegylated interferon alfa is administered, and the medicament containing the silibinin component is also administered during the second period, preferably parenterally. Preferably, during the third period said other medicament which preferably contains ribavirin and/or pegylated interferon alfa is administered, but the medicament containing the silibinin component is not administered during the third period, i.e., only said other medicament is administered.

Preferred embodiments $G_1$ to $G_{15}$ of the triphasic treating regimen are summarized in the table here below:

| no. of days | $G_1$ | $G_2$ | $G_3$ | $G_4$ | $G_5$ | $G_6$ | $G_7$ | $G_8$ | $G_9$ | $G_{10}$ | $G_{11}$ | $G_{12}$ | $G_{13}$ | $G_{14}$ | $G_{15}$ |
|---|---|---|---|---|---|---|---|---|---|---|---|---|---|---|---|
| first period | ≥1 | ≥1 | ≥2 | ≥1 | ≥1 | ≥2 | ≥2 | ≥2 | ≥3 | ≥4 | ≥5 | ≥6 | ≥7 | ≥14 | ≥14 |
| second period | ≥1 | ≥2 | ≥1 | ≥1 | ≥2 | ≥2 | ≥1 | ≥2 | ≥3 | ≥4 | ≥5 | ≥6 | ≥7 | ≥7 | ≥14 |
| third period | ≥1 | ≥1 | ≥1 | ≥2 | ≥2 | ≥1 | ≥2 | ≥2 | ≥3 | ≥4 | ≥5 | ≥6 | ≥7 | ≥7 | ≥7 |

In yet another preferred embodiment, the treating regimen according to the invention comprises three phases which follow one another consecutively, namely a first period, a second period and a third period. Preferably, during the first period another medicament is administered which preferably contains ribavirin and/or pegylated interferon alfa, and the medicament containing the silibinin component is not administered during the first period. During the second period said another medicament which preferably contains ribavirin and/or pegylated interferon alfa is still administered, and the medicament containing the silibinin component is also administered (co-administered) during the second period, preferably parenterally. Preferably, during the third period said other medicament which preferably contains ribavirin and/or pegylated interferon alfa is administered, but the medicament containing the silibinin component is not administered during the third period, i.e., only said other medicament is administered. In other words, according to this preferred embodiment, said other medicament which preferably contains ribavirin and/or pegylated interferon alfa is administered continuously, and during an interim period (=second period) the medicament containing the silibinin component is co-administered, preferably parenterally.

Preferred embodiments $H_1$ to $H_{15}$ of the triphasic treating regimen are summarized in the table here below:

| no. of days | $H_1$ | $H_2$ | $H_3$ | $H_4$ | $H_5$ | $H_6$ | $H_7$ | $H_8$ | $H_9$ | $H_{10}$ | $H_{11}$ | $H_{12}$ | $H_{13}$ | $H_{14}$ | $H_{15}$ |
|---|---|---|---|---|---|---|---|---|---|---|---|---|---|---|---|
| first period | ≥1 | ≥1 | ≥2 | ≥1 | ≥1 | ≥2 | ≥2 | ≥2 | ≥3 | ≥4 | ≥5 | ≥6 | ≥7 | ≥14 | ≥14 |
| second period | ≥1 | ≥2 | ≥1 | ≥1 | ≥2 | ≥2 | ≥1 | ≥2 | ≥3 | ≥4 | ≥5 | ≥6 | ≥7 | ≥7 | ≥14 |
| third period | ≥1 | ≥1 | ≥1 | ≥2 | ≥2 | ≥1 | ≥2 | ≥2 | ≥3 | ≥4 | ≥5 | ≥6 | ≥7 | ≥7 | ≥7 |

Figure 10:
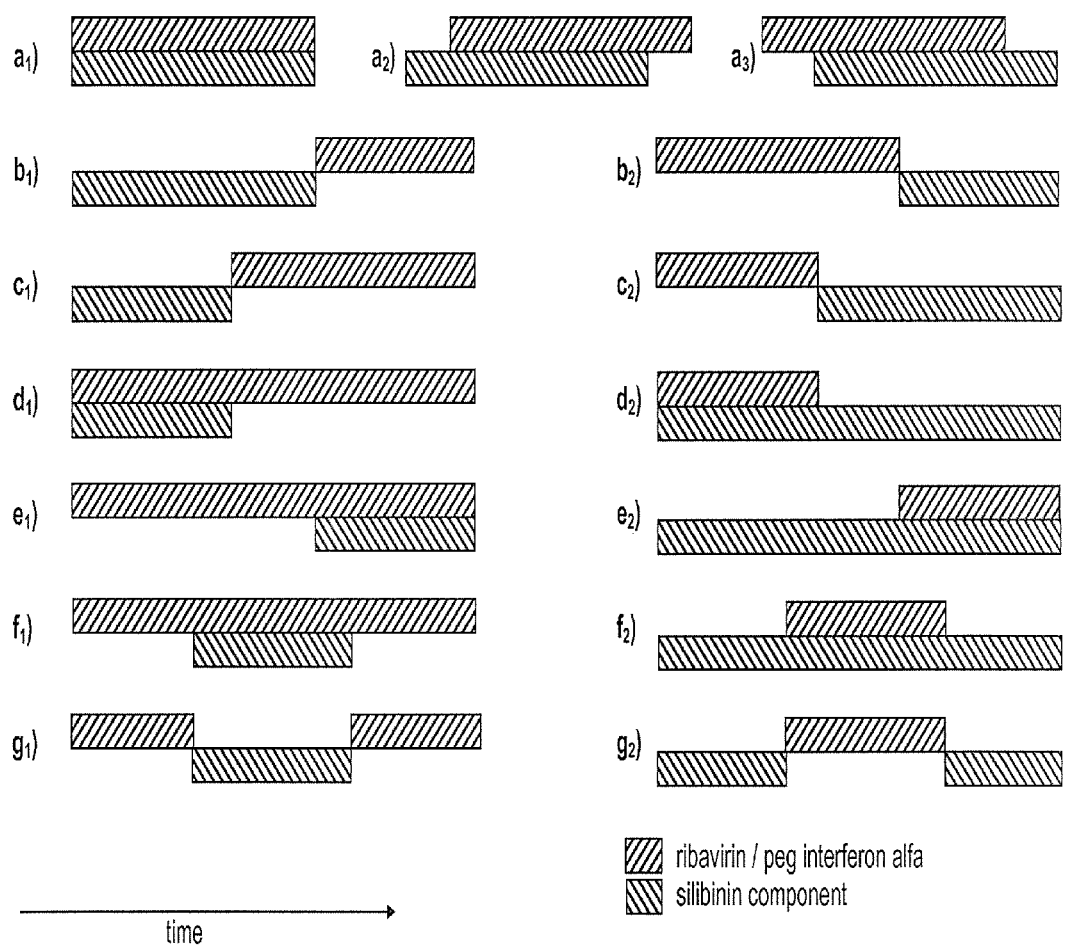
FIG. 10 displays schematically various modes of co-administration of ribavirin and/or pegylated interferon alfa and the medicament containing the silibinin component.
Figure 10:
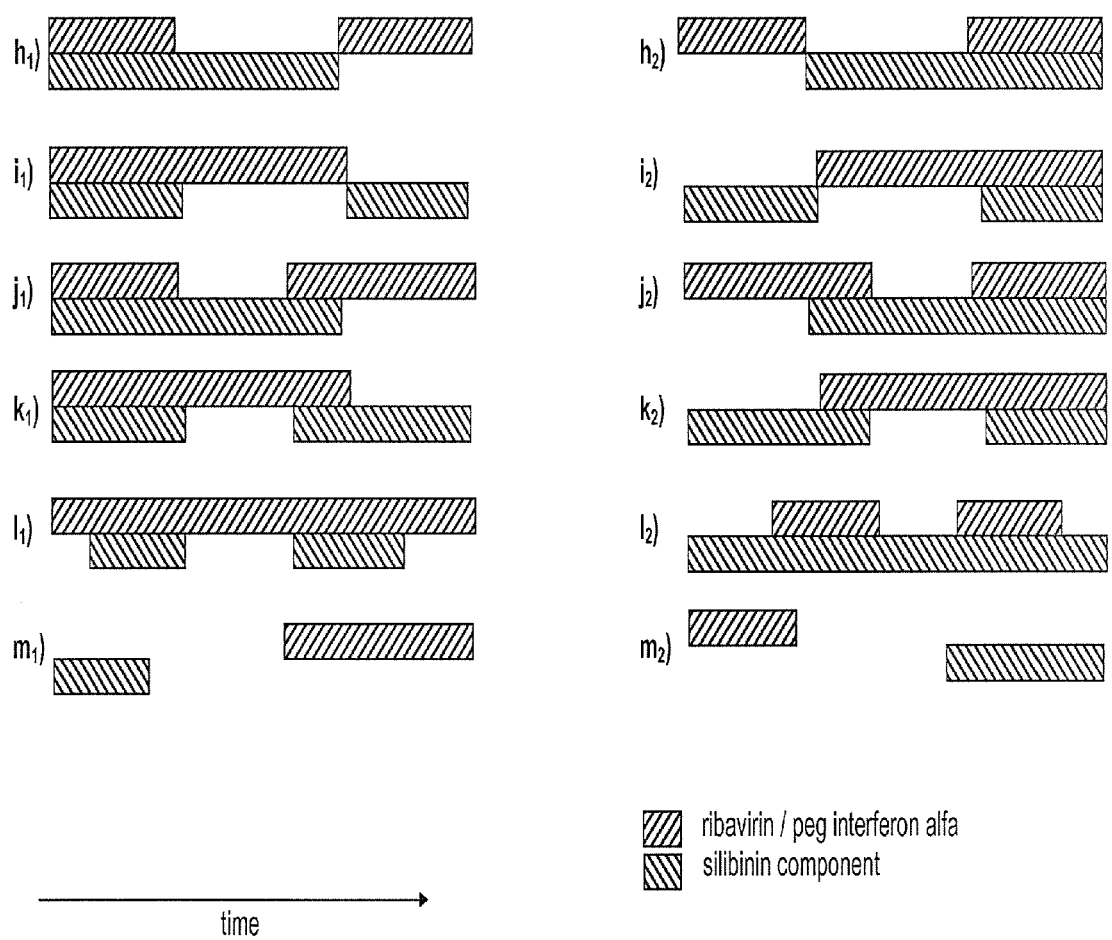

FIG. 10 visualizes various modes of co-administration of ribavirin and/or pegylated interferon alfa and the medicament containing the silibinin component (embodiments $a_1$) to $m_2$)). Each bar refers to a time period of administration. For example, according to embodiment $f_1$), administration commences with ribavirin/peg interferon alfa and continues. During an interim period, the silibinin component is co-administered.

A further aspect of the invention relates to a medicament as described above, preferably adapted for parenteral administration, for treating viral hepatitis as described above.

A still further aspect of the invention relates to a kit comprising at least one medicament according to the invention, which contains a silibinin component, and at least one other medicament. Both the medicament according to the invention, which contains a silibinin component, and the other medicament are described above, such that all preferred embodiments analogously also apply for the kit according to the invention.

In a preferred embodiment, the kit contains as many medicaments (individual dose units) as are necessary in order to carry out a sequential therapy, the medicament which contains the silibinin component initially being administered for a first period and subsequently the other medicament being administered for a second period. Preferably, the first period comprises at least 2 days, more preferably at least 3 days, even more preferably at least 4 days, most preferably at least 5 days and in particular at least 6 days. Preferably, the second period comprises more days than the first period. Preferably, the second period comprises at least 2 days, more preferably at least 3 days, even more preferably at least 4 days, most preferably at least 5 days and in particular at least 6 days.

In a particularly preferred embodiment, the invention relates to the use of a silibinin component, preferably of a silibinin ester, for the production of a medicament, which is formulated for parenteral administration, for the treatment of viral hepatitis C in non-responders with regard to ribavirin/interferon therapy, i.e., in patients who do not respond to immunomodulatory/antiviral combination therapy such as ribavirin/interferon therapy.

A further aspect of the invention relates to a silibinin component, preferably a silibinin ester, preferably for parenteral administration, for the treatment of viral hepatitis, preferably hepatitis C. Preferred embodiments of the aspect of the invention become evident from the above description of the preferred embodiments of the other aspects of the invention and thus, are not repeated.

A further aspect of the invention relates to the treatment of viral hepatitis, preferably hepatitis C, comprising the administration, preferably the parenteral administration, of a pharmaceutically effective amount of a silibinin component, preferably of a silibinin ester, to a subject in need thereof. Preferred embodiments of the aspect of the invention become evident from the above description of the preferred embodiments of the other aspects of the invention and thus, are not repeated.

The following examples further illustrate the invention but are not to be construed as limiting its scope.

Example 1

The silibinin component was administered parenterally in form of the silibinin C-2',3-bis(hydrogensuccinate) (Legalon Sil®, Madaus, Köln) (in the following referred to as "silibinin").

Patients and Methods:

| Patients | Protocol 1 | Protocol 2 |
|---|---|---|
| N (male/female) | 16 (14/2) | 20 (17/3) |
| Mean age (years ± SD) | 49.9 ± 9.7 | 52.7 ± 12.8 |
| Genotype (1/2/4) | 15/—/1 | 17/1/2 |
| Fibrosis stage: | | |
| 0-2 | 3 | 10 |
| 3-4 | 13 | 7 |
| Not available | — | 3 |
| preceding therapy* | | |
| PEG-interferon-alfa2a/RBV | 14 | 18 |
| PEG-interferon-alfa2b/RBV | 2 | 4 |
| Log drop at week 12 of preceding therapy | | |
| >2** | 3 | 4 |
| 1-2 | 4 | 1 |
| <1 | 5 | 12 |
| not available | 2 | 3 |
| | 14 | 18 |
| | 2 | 4 |

*some patients had more than one treatment cycle
**all were positive at week 24

Patients with previous nonresponse to full dose of peginterferon/ribavirin combination therapy were selected for these studies. Nonresponse was defined by the lack of a >2 log drop of viral load after 12 weeks of therapy and/or by not achieving an end of treatment response. Patients were required to have a liver biopsy done within 2 years prior inclusion into this study. Standard inclusion/exclusion criteria for peginterferon/ribavirin therapy were applied.

Study Protocol:

During a screening phase within 35 days prior to the first dose of study drug eligibility of patients according to inclusion/exclusion criteria was established. All patients had at least one quantitative HCV-RNA tests within the 6 months before the screening phase.

Protocol 1:

Patients first received daily 10 mg/kg silibinin (Legalon Sil®, Madaus, Köln) infused over 4 hrs for 7 consecutive days. On day 1 blood was drawn for determination of oxidative stress parameters at baseline, every 30 minutes during the infusion and 2 hours after the end of the infusion. On day 8 treatment was changed to 140 mg silymarin (Legalon®, Madaus, Köln) TID per os in combination with 180 μg/wk PegIFNa-2a (PEGASYS®; Roche, Basel) and 1-1.2 g/d ribavirin (COPEGUS®; Roche, Basel).

Protocol 2:

After obtaining the results for the first protocol, treatment with silibinin was extended for 2 weeks and different doses of silibinin were administered. Patients first received daily 5, 10, 15 or 20 mg/kg silibinin infused over 4 hrs for 14 consecutive days. On day 8 treatment with 180 μg/wk PegIFNa-2a and 1-1.2 g/d ribavirin was started. After day 14 patients received 280 mg silymarin (Legalon®, Madaus, Köln) TID per os. During the 14 day infusion period blood was obtained daily for determination of viral load.

In both protocols in case of intolerance to PEG-IFN alfa2a or ribavirin, standard dose adjustment guidelines were used. Antiviral combination therapy was given for a total of 24 weeks (with the Option to stop treatment in patients without a >2 log drop at week 12); virologic responders at week 24 were offered to continue treatment for further 48 weeks. After end of the infusion period patients were tested after weeks 2, 4, and then monthly till the end of therapy at week 24.

The protocol was approved by the ethics committee of the Medical University of Vienna. The details of the study were explained to the patients and all signed an informed consent.

Methods:

Serum HCV RNA level was determined by the TaqMan PCR assay (Cobas Ampliprep/Cobas TaqMan HCV Test; limit of detection, 15 IU/mL, Roche Diagnostics).

Reactive oxidative metabolites in blood were measured by the d-ROMs test (Reactive Oxygen Metabolites derived compounds; Diacron, Grosseto, Italy), and the amounts of antioxidants by the BAP test (Biological Antioxidant Potential; Diacron, Grosseto, Italy) using the portable, free radicals determination system (FRAS 4, SEAC, Calenzano, Italy) before, every 30 minutes during (on day 1) and 2 hours after the silibinin infusions. The d-ROM test measures reactive oxygen metabolites (primarily hydroperoxides) released from plasma proteins by an acidic buffer, which in presence of iron generate alkoxyl and peroxyl radicals, according to the Fenton's reaction. Such radicals, in turn, are able to oxidize an alkyl-substituted aromatic amine (N,N-dietylparaphenylendiamine), thus producing a pink-coloured derivative which is photometrically quantified at 505 nm. Results for reactive oxidative metabolites are expressed as Caratelli Units (Ucarr; normal: 250-300, 1 Ucarr=0.08 mg hydrogen peroxide/di). The BAP test measures the decolouration intensity of a ferric chloride solution mixed with a thiocyanate derivative by the added plasma sample photometrically at 505 nm, which is proportional to the ability to reduce ferric ions by the amounts of antioxidants in plasma (normal >2200 pM). The description of the assays by the manufacturer does not specify which substances are actually measured.

Statistics:

Originally, the primary outcome variable was the virologic response defined as the percentage of patients being PCR negative at end of treatment (week 24). Secondary efficacy variables were virologic response rates at week 12, safety and tolerability of treatment with PEG-IFN/ribavirin/silymarin, Quality of life at baseline, at week 24, week 48, week 72 (SF-36, Fatigue Severity Scale), and the oxidative status after silibinin infusions. Due to the unexpected strong virologic response after 7 days of silibinin infusions the recruitment was halted and the study was redesigned based on virologic response parameters using longer infusion periods and higher doses of silibinin. For the original study the sample size was estimated based on Gehan's two stage design. According to previous studies, a response rate of >10% seems to warrant further investigation of the treatment regime. 29 patients had to be recruited in the first stage accordingly (error probability 11=5%).

Results:

Protocol 1:

Sixteen pedigreed nonresponders (for details see table above) were included. All patients had received full dose treatment with pegylated interferon (12 peginterferon alfa 2a, 2 peginterferon alfa 2b) and ribavirin (1000-1200 mg/d) for at least 12 weeks. Parameters of oxidative stress measured did not change during silibinin infusions (FIG. 1).

Figure 2:
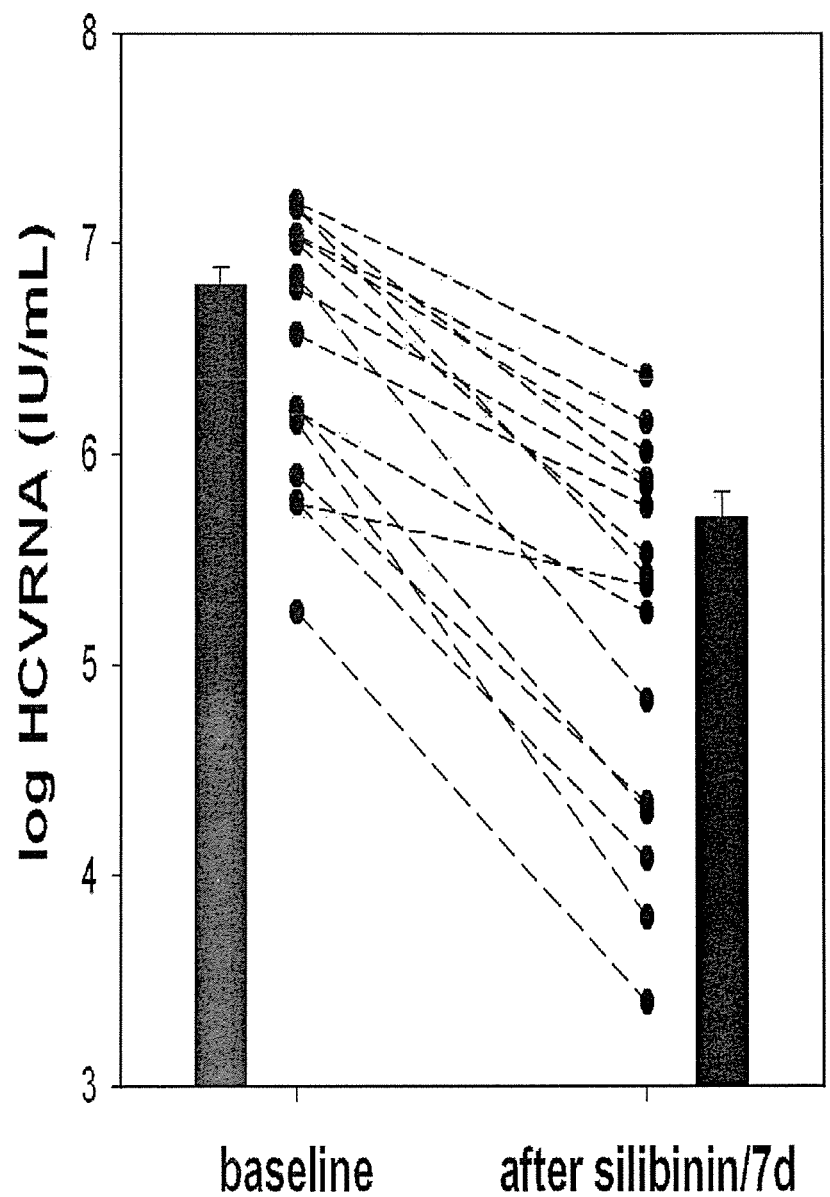
FIG. 2: Example 1, Study 1: HCV-RNA (log IU/ml; mean±SD) before (day 1) and after 7 days of iv 10 mg/kg silibinin component/day.
Figure 3:
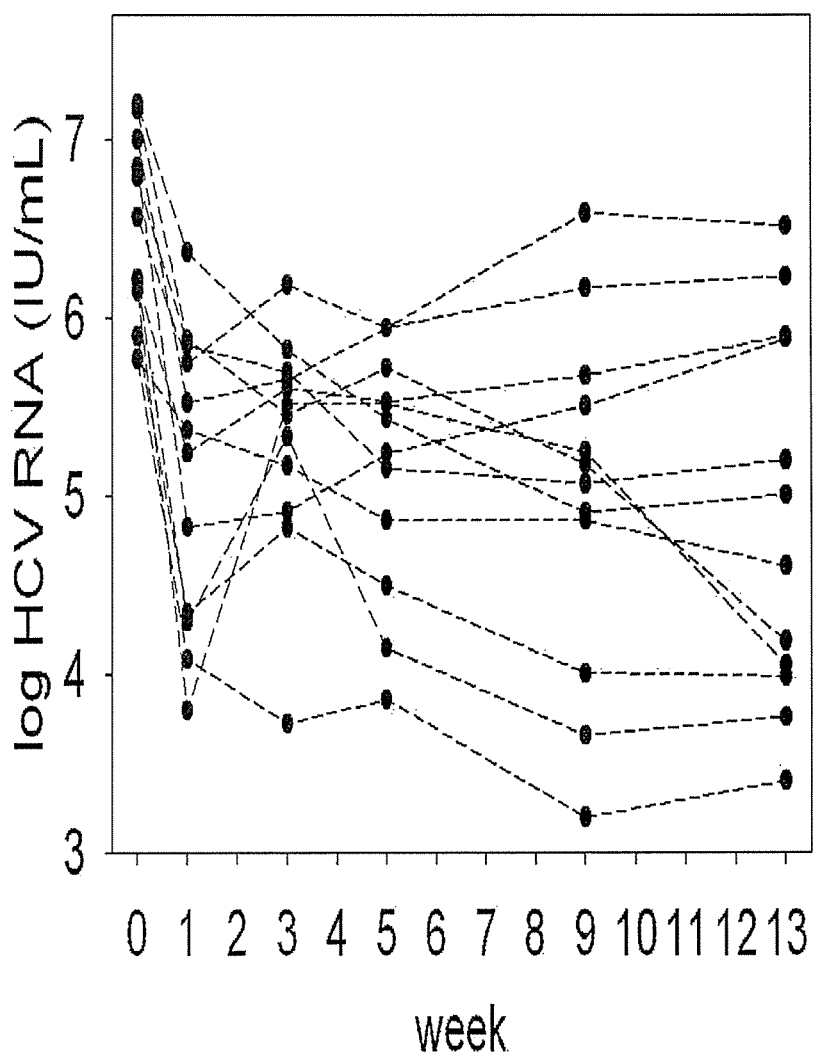
FIG. 3: Example 1, Study 1: Changes in HCV-RNA after iv. administration of 10 mg/kg/day silibinin component for 7 days, followed by combination therapy with peginterferon alfa 2a/ribavirin and 140 mg silymarin TID.

Serum HCV RNA declined in all patients an iv. SIL-monotherapy (FIG. 2) (baseline: 6.59±0.53, day 8: 5.26±0.81 log IU/ml, [mean±SD], p<0.001) with a mean log decline of 1.32±0.55 within one week. In parallel, ALT decreased from 162±133 to 118±107 U/l (p=0.004). In all patients HCV RNA remained detectable at initiation of PegIFN/RBV therapy. Three patients declined PEGIFN/RBV combination therapy. In 11 of the remaining 13 patients HCV-RNA increased again after the end of the silibinin infusions in spite of initiation of PegIFN/RBV. At week 12 all patients were still HCV-RNA positive, but 5 patients had a >2 log drop and continued treatment (FIG. 3). None of them became HCV-RNA negative at week 24, one patient had a 5.5 log drop and continues treatment by own wish.

Protocol 2:

Twenty pedigreed nonresponders (for details see table above) were included. All patients received full dose treatment with pegylated interferon (18 peginterferon alfa 2a, 4 peginterferon alfa 2b; 2 patients received 2 treatment courses) and ribavirin (1000-1200 mg/d) for at least 12 weeks.

Figure 4:
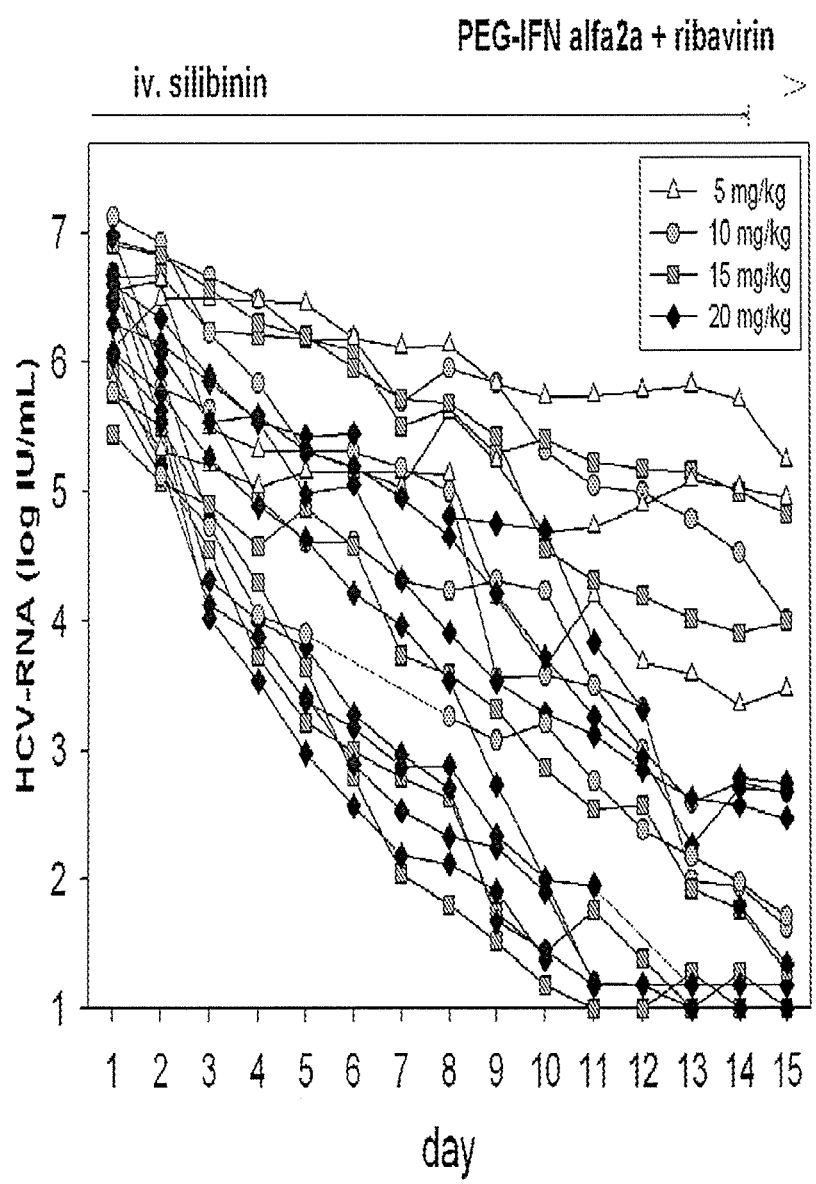
FIG. 4: Example 1, Study 2: Changes in HCV-RNA during iv. administration of silibinin component at various doses for 14 days, followed by combination therapy with peginterferon alfa 2a/ribavirin which was started on day 8.

FIG. 4 shows the viral kinetics in these patients. Viral load declined continuously. After 7 days of silibinin monotherapy the 5 mg/kg dose was marginally effective (n=3, log drop 0.55±0.5), whereas the 10 mg/kg (n=19 [including the patients in protocol 1], log drop 1.41±0.59), 15 mg/kg (n=5, log drop 2.11±1.15) and 20 mg/day doses (n=9, 3.02±1.01) led to a highly significant decrease in viral load (p<0.001).

Figure 5:
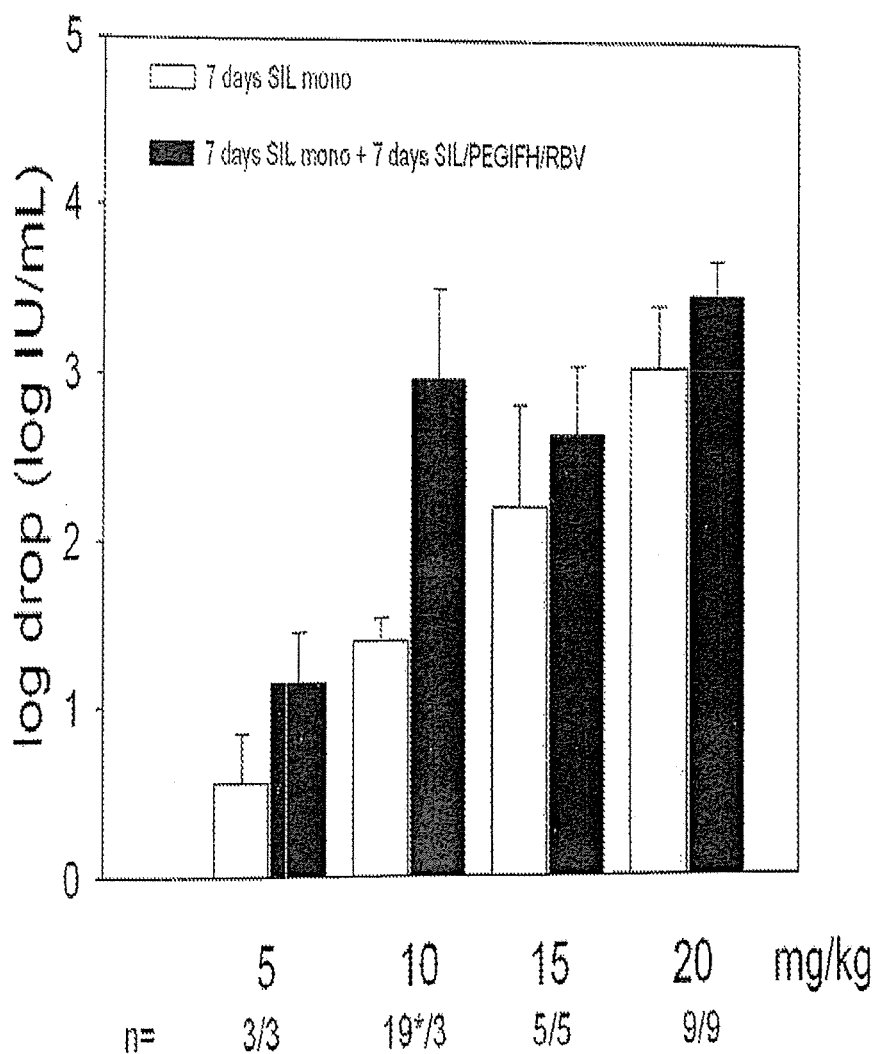
FIG. 5: Example 1, Study 2: Mean (±SD) decrease of HCV-RNA during 7 day iv. administration of silibinin component monotherapy and 7 days of iv. silibinin component in combination with peginterferon alfa 2a/ribavirin at various doses.
Figure 6:
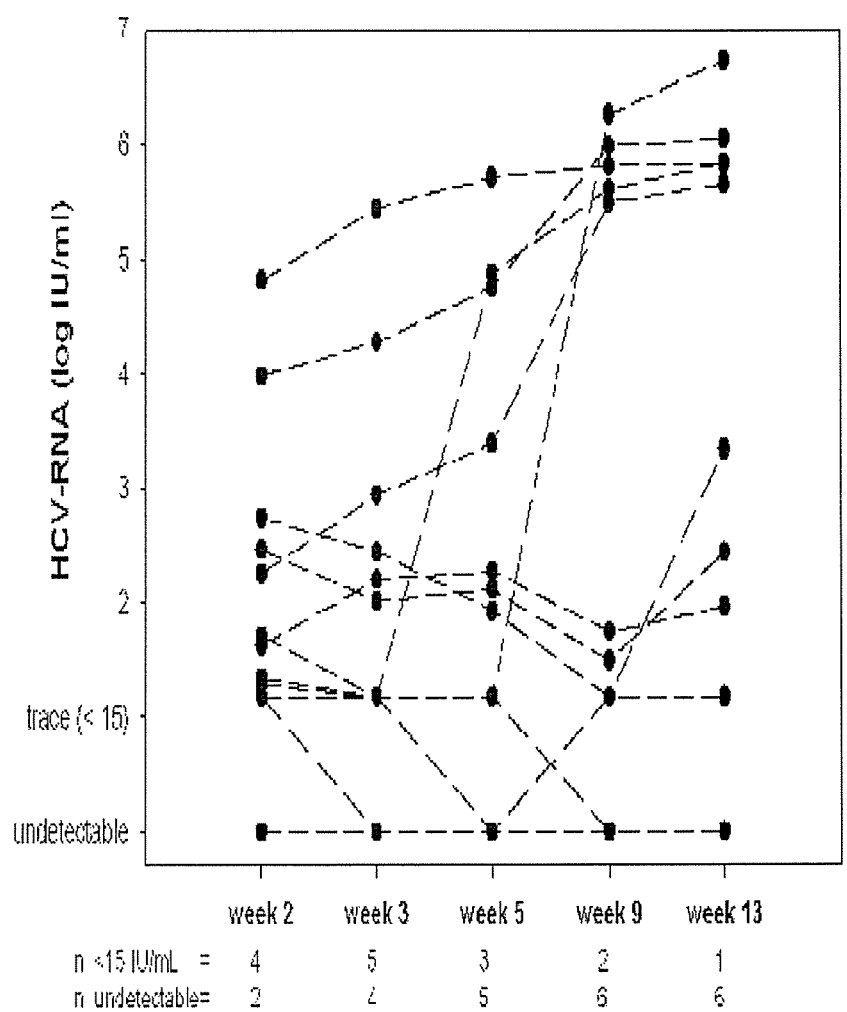
FIG. 6: Example 1, Study 2: Changes in HCV-RNA after the end of iv. silibinin (week 2) in the 14 patients who received 15 or 20 mg/kg/silibinin/d. Combination therapy with peginterferon alfa 2a/ribavirin was started an day 8 and 280 mg silymarin TID an day 15.

After 1 week of combined silibinin and peginterferon/ribavirin therapy viral load decreased further (log drop: 5 mg/kg: 1.63±0.78; 10 mg/kg: 4.16±1.28; 15 mg/kg 3.69±1.29; 20 mg/kg 4.8±0.89; all p<0.0001 vs. baseline) (FIG. 5). Two of the 5 patients in the 15 mg/kg group and 4 of the 9 patients in the 20 mg/kg group had HCVRNA<15 IU at day 15. HCV-RNA was <15 IU/ml in 8 and 7 patients at week 4 (week 5 of the study protocol) and week 12 (week 13 of the study protocol) after start of PEGIFN/RBV, respectively. Antiviral combination therapy was continued for all patients (FIG. 6).

Safety:

Silibinin was generally well tolerated. Five patients complained of mild gastrointestinal symptoms (abdominal pain:

5, diarrhea: 2, nausea 1), two of headache and one of arthralgia. All of these were rated to be mild by the patients and subsided after the end of the infusions; changes in the dosing were not required. All patients in the 15 and 20 mg/kg groups noted a sensation of heat when the infusion was started, which subsided within 30 minutes without treatment. No SAEs occurred. On monotherapy no changes of hemoglobin, leucocytes, platelets, and creatinine were observed. The typical side effects of antiviral combination therapy were observed (including one patient suffering of increasing dyspnoea due to hemophilus influenzae induced pneumonia, requiring termination peginterferon/ribavirin therapy after 8 weeks).

This example demonstrates that parenteral administration of silibinin (C-2',3-bis(hydrogensuccinate)) has a marked antiviral activity against the hepatitis C virus. These observations demonstrate the potential of this drug for treatment of chronic hepatitis C, particularly in non-responders.

It has been surprisingly found that iv. silibinin (C-2',3-bis (hydrogensuccinate)) is a potent antiviral agent in patients with chronic hepatitis C not responding to standard antiviral combination therapy. Intravenous silibinin was well tolerated, no serious adverse effects were observed. The most commonly reported side effect was a transient sensation of heat. The antiviral effect was dose dependent but was not maintained after the end of the infusion period by the oral administration of silymarin.

In comparison, similar amounts of silymarin given orally have no effect on HCV-load (A Gordon at al., J Gastroenterol Hepatol. 2006, 21, 275-80) reflecting differences in bioavailabilty and metabolism of silibinin resulting in far lower plasma levels. After oral dosing silymarin flavonolignans are quickly glucuronidated and rapidly eliminated with short half-lives (Z Wen et al., Drug Metab Dispos. 2008, 36(1), 65-72).

Example 2

Patients were continuously treated with 180 μg peginterferon alfa 2a and weight based ribavirin. In spite of this treatment, five patients were HCV-RNA positive after 24 weeks of therapy: Three male patients and two female patients; four patients with HCV genotype 1 and one patient with HCV genotype 3a; three patients with cirrhosis.

Four patients can be regarded as naïve, whereas one patient can be regarded as relapser with respect to two previous therapies (24 and 48 weeks).

In the course of the ongoing treatment with 180 μg peginterferon alfa 2a and weight based ribavirin, all patients were treated at least once for 14 consecutive days with 20 mg/kg/d silibinin iv. During this period, combination therapy with peginterferon/ribavirin was continued.

All 5 patients became HCV-RNA negative.

Figure 7:
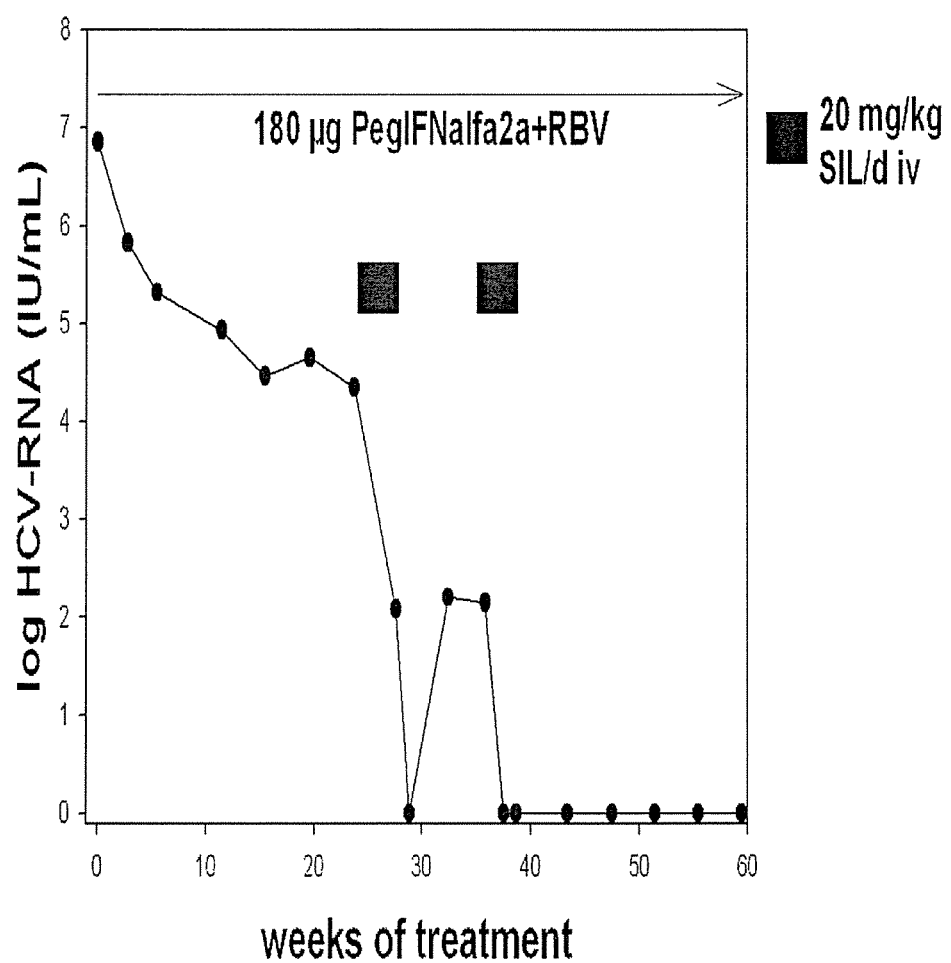
FIG. 7: Example 2, individual patient, changes in HCV-RNA after iv. administration of 20 mg/kg/day silibinin component during two administration intervals comprising 14 consecutive days, the first i.v. administration interval commencing in week 24 and the second administration interval commencing in week 35, during a continuous combination therapy with 180 µg peginterferon alfa 2a/ribavirin for 60 weeks.

FIG. 7 shows the result for one individual patient (male, 55 years). As can be seen, peginterferon/ribavirin merely causes a decline of the viral load from about log 7 IU/mL to about log 4.5 IU/mL after 24 weeks. Co-treatment with 20 mg/kg/day i.v. silibinin bis(hydrogensuccinate) for 14 days, however, lead to a dramatic decrease of the viral load from about log 4.5 IU/mL to a value below the detection limit. After the first administration interval of parenteral silibinin bis(hydrogensuccinate), viral load increased again to about 2 IU/mL, which could, however, permanently be depressed below the detection limit by a second co-treatment with 20 mg/kg/day i.v. silibinin bis(hydrogensuccinate) for 14 days.

Figure 8:
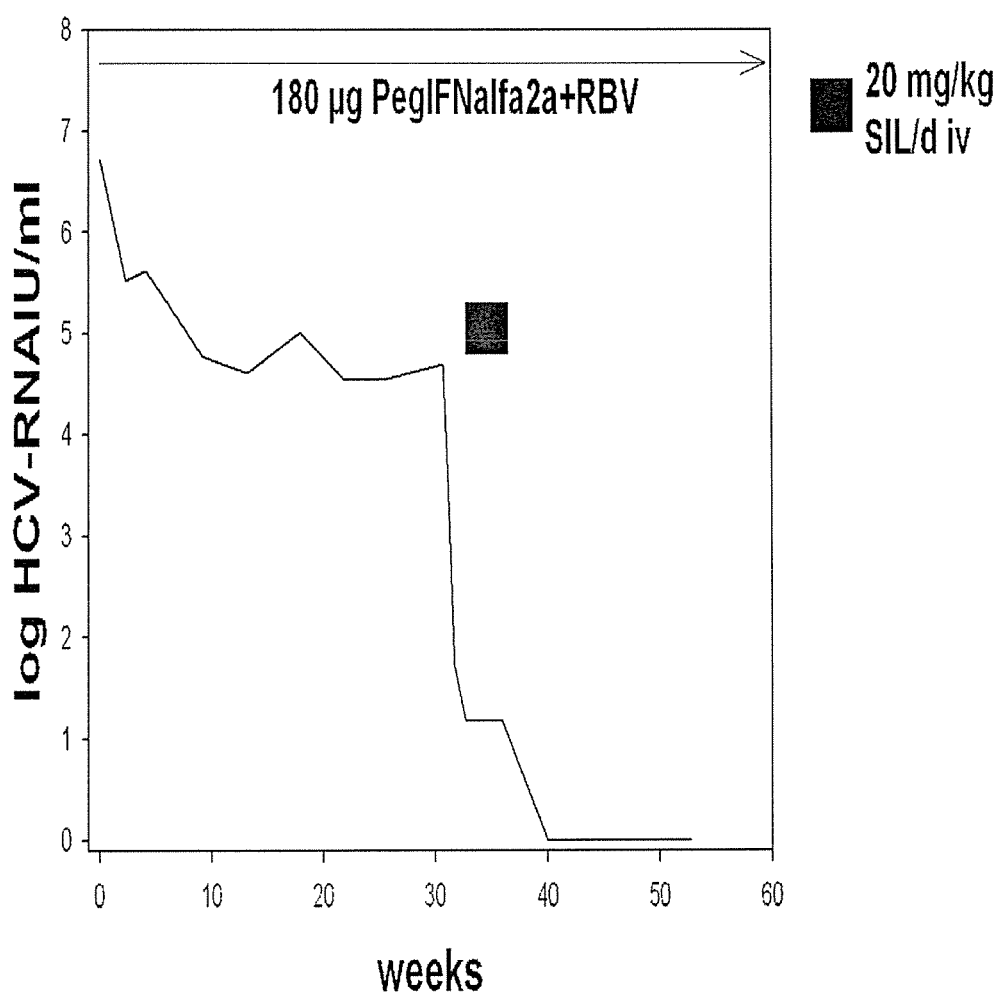
FIG. 8: Example 2, individual patient, changes in HCV-RNA after iv. administration of 20 mg/kg/day silibinin component during an administration interval comprising 14 consecutive days and commencing in week 32 during a continuous combination therapy with 180 µg peginterferon alfa 2a/ribavirin for 60 weeks.

FIG. 8 shows the result for another individual patient (female, 44 years). As can be seen, peginterferon/ribavirin merely causes a decline of the viral load from about log 7 IU/mL to about log 5 IU/mL after 30 weeks. Co-treatment with 20 mg/kg/day i.v. silibinin bis(hydrogensuccinate) for 14 days after 30 weeks, however, lead to a dramatic and permanent decrease of the viral load from about log 4 IU/mL to a value below the detection limit.

Figure 9:
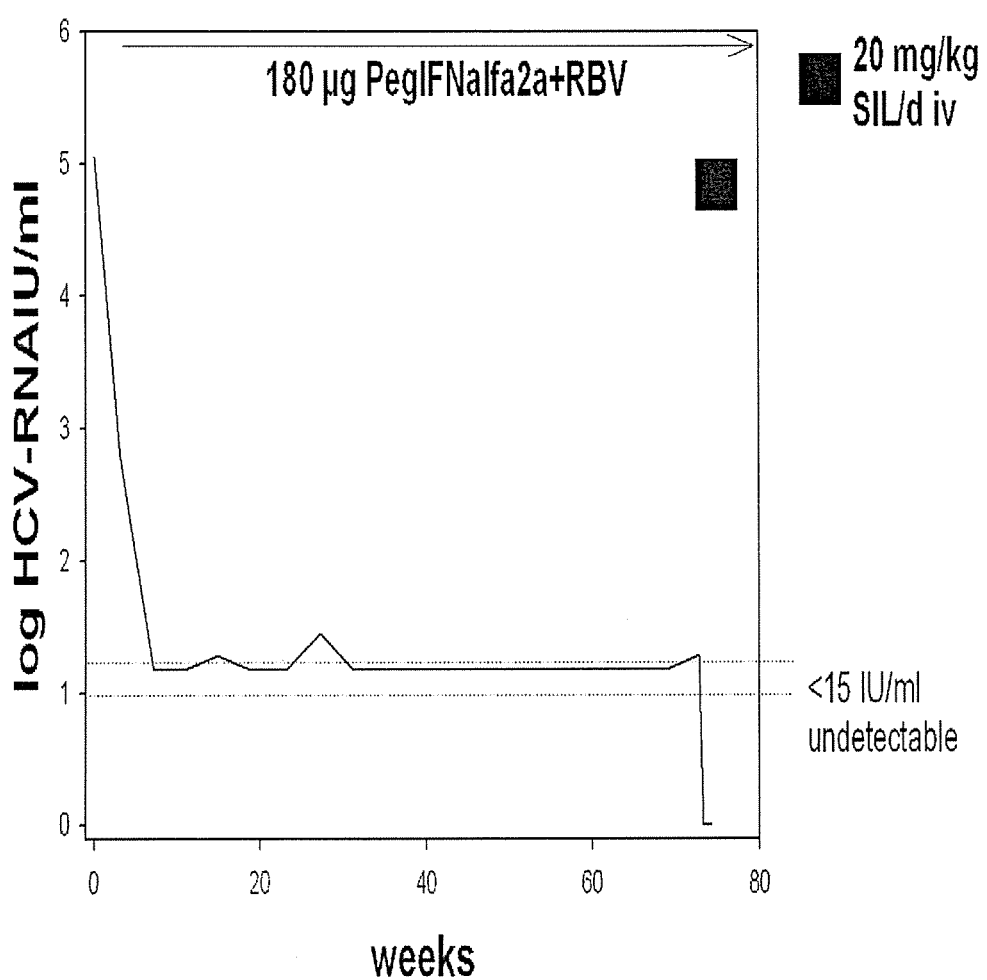
FIG. 9: Example 2, individual patient, changes in HCV-RNA after iv. administration of 20 mg/kg/day silibinin component during an administration interval comprising 14 consecutive days and commencing in week 72 during a continuous combination therapy with 180 µg peginterferon alfa 2a/ribavirin for 80 weeks.

FIG. 9 shows the result for one individual patient (male, 52 years). As can be seen, peginterferon/ribavirin causes an efficient decline of the viral load from about log 5 IU/mL to a value close to the detection limit of <15 IU/mL. Co-treatment with 20 mg/kg/day i.v. silibinin bis(hydrogensuccinate) for 14 days after 72 weeks caused a further decrease of the viral load far below the detection limit.

These clinical tests demonstrate that parenteral treatment with a silibinin component for a comparatively short time interval supports and significantly improves conventional treatment by peginterferon/ribavirin. It appears that parenteral administration of silibinin component (re)activates the patients' susceptibility to conventional treatment by peginterferon/ribavirin (FIGS. 7 and 8) and/or enhances the antiviral effect of conventional treatment by peginterferon/ribavirin (FIG. 9).

Example 3

An in vivo study was performed to characterize plasma concentration/time profiles of silibinin in 8 patients suffering from chronic hepatitis C who received 7 days i.v. infusion treatment with 20 mg silibinin/kg body weight (Legalon® SIL). For multiple doses of 20 mg/kg body weight, plasma concentration/time profiles and PK parameters of free and total silibinin had been observed on day 1 (=single dose conditions) and were compared with those on day 7 (=expected steady state conditions).

Analytical Procedure:

The study samples were analyzed using a validated HPLC-UV method. During the assay period the analytical procedure was validated by two calibration curves per analytical run. Inspection of the chromatograms of the data presented on calibration curves and quality control samples indicates that the result of the determinations of total and free silibinin A and silibinin B concentrations for the study is reliable.

The PK characteristics are summarized in the following table:

|  | day 1 | | day 7 | |
| --- | --- | --- | --- | --- |
|  | Silibinin A | Silibinin B | Silibinin A | Silibinin B |
| Total Silibinin | | | | |
| AUC(0-∞) [h ng/ml] | 61733 ± 27489 | 13745 ± 76040 | — | — |
| AUC(0-$t_z$) [h ng/ml] | 50019 ± 20048 | 109038 ± 51342 | — | — |
| AUCss [h ng/ml] | — | — | 84299 ± 25111 | 150780 ± 47780 |
| $C_{min}$ [h ng/ml] | — | — | 1967 ± 831 | 3311 ± 1426 |
| $C_{max}$ [ng/ml] | 4550 ± 928 | 9539 ± 2843 | 5791 ± 977 | 11083 ± 2269 |

-continued

|  | day 1 | | day 7 | |
|---|---|---|---|---|
|  | Silibinin A | Silibinin B | Silibinin A | Silibinin B |
| $C_{av}$ [ng/ml] | — | — | 3512 ± 1046 | 6282 ± 1991 |
| $t_{1/2}$ [ng/ml] | 8.30 ± 2.26 | 8.29 ± 2.98 | 13.32 ± 3.66 | 12.02 ± 2.91 |
| HVD [h] | 9.28 ± 3.36 | 9.47 ± 3.29 | 15.20 ± 4.09 | 13.17 ± 3.62 |
| MRT [h] | 13.17 ± 3.74 | 13.44 ± 4.39 | 19.22 ± 5.28 | 17.34 ± 4.20 |
| CL [ml/(h kg)] | 0.435 ± 0.336 | 0.233 ± 0.237 | 0.269 ± 0.128 | 0.156 ± 0.091 |
| Vz [ml/kg] | 4.7 ± 1.3 | 2.4 ± 1.1 | 4.67 ± 0.73 | 2.43 ± 0.55 |
| $t_{max}$ [h] | 4.14 ± 0.18 | 4.17 ± 0.18 | — | — |
| % PTF [%] | — | — | 121.89 ± 54.43 | 137.59 ± 52.51 |
| Free Silibinin | | | | |
| AUC(0-∞) [h ng/ml] | 3614 ± 1648 | 753 ± 397 | — | — |
| AUC(0-$t_z$) [h ng/ml] | 3302 ± 1551 | 559 ± 339 | — | — |
| AUCss [h ng/ml] | — | — | 4095 ± 1942 | 1041 ± 627 |
| $C_{min}$ [h ng/ml] | — | — | 59 ± 40 | 3.3 ± 8.7 |
| $C_{max}$ [ng/ml] | 316 ± 108 | 90 ± 44 | 315 ± 119 | 120 ± 54 |
| $C_{av}$ [ng/ml] | — | — | 171 ± 81 | 43 ± 26 |
| $t_{1/2}$ [ng/ml] | 4.58 ± 1.35 | 5.16 ± 4.96 | 6.85 ± 1.29 | 4.35 ± 1.66 |
| HVD [h] | 10.12 ± 4.29 | 6.09 ± 2.14 | 11.87 ± 2.64 | 7.17 ± 1.63 |
| MRT [h] | 8.49 ± 2.64 | 8.81 ± 6.12 | 9.88 ± 1.86 | 6.27 ± 2.39 |
| CL [ml/(h kg)] | 7.0 ± 4.2 | 44.8 ± 42.5 | 5.9 ± 2.9 | 26.8 ± 16.7 |
| Vz [ml/kg] | 51.4 ± 12.7 | 285.8 ± 163.9 | 55.3 ± 18.5 | 140.4 ± 49.0 |
| $t_{max}$ [h] | 3.73 ± 1.22 | 4.03 ± 0.04 | — | — |
| % PTF [%] | — | — | 164.00 ± 45.33 | 305.24 ± 80.46 |

Example 4

An in vitro study was performed to assess the cytotoxic potential of silymarin, silibinin, silibinin bis(hydrogensuccinate) disodium salt, and succinic acid by means of the XTT test using the mouse cell line L929 (cf. D. A. Scudiero et al., Cancer Res. 48, 4827-33; O, S. Weislow et al., J. Natl. Cancer Inst., 81, 577-86; N. W. Roehm et al., J. Immunol. Methods, 142).

The following concentrations of the test items were tested: 9.77, 19.53, 39.06, 78.13, 156.25, 312.5, 625, 1250 µg/mL. Complete medium (RPMI 1640 containing 10% (v/v) FCS) was used as negative control. The solvent control for the test item was RPMI 1640 medium containing 10% (v/v) FCS) and 1% DMSO. The solvent control for the positive control was also RPMI 1640 medium containing 10% (v/v) FCS and 10.0% (v/v) deionized water. SDS was used as positive control. The following concentrations were applied: 3.125, 6.25, 12.5, 25, 50, 100, 125, 250 µg/mL. The incubation time was 24 hours at 37±1.5° C.

The negative control and the solvent control showed no reduction in cell viability. The positive control (SDS) induced a distinct dose-related reduction in cell viability.

Toxic effects were observed following incubation with silymarin from 39.06 µg/mL up to the highest tested concentration (1250 µg/mL). The calculated $XTT_{50}$ value is 35.2 µg/mL.

Toxic effects were observed following incubation with silibinin from 78.13 µg/mL up to the highest tested concentration (1250 µg/mL). The calculated $XTT_{50}$ value is 67.5 µg/mL.

No relevant cytotoxic effects were observed following incubation with silibinin-bis(hydrogensuccinate) sodium salt up to the highest tested concentration (1250 µg/mL). Due to the lack of cytotoxicity, a $XXT_{50}$ value could not be calculated.

No relevant cytotoxic effects were observed following incubation with succinic acid up to the highest tested concentration (1250 µg/mL). Due to the lack of cytotoxicity, a $XXT_{50}$ value could not be calculated.

These experiments revealed that under the given conditions, the cytotoxic potential of silymarin is nearly 100% higher than the cytotoxic potential of silibinin. Thus, it can be expected that silibinin can be administered in higher doses than silymarin without causing serious adverse side effects.

Example 5

NS5B RNA-dependent RNA polymerase (RdRp) is an essential enzyme fir viral replication (cf. S. B. Hwang et al., Virology 1997, 227, 439-46). The following pure compounds were tested in a cell-free enzyme assay for the detection of HCV RdRp activity: silibinin A, silibinin B, isosilibinin A, isosilibinin B, silichristin, silidianin, and the silibinin ester silibinin-C-2'',3-bis(hydrogensuccinate) disodium (active ingredient of Legalon® SIL).

Stock solutions (100 mM) of the compounds in 100% DMSO were prepared. The concentration of DMSO in all reactions was kept constant at 5%. Target enzyme for the study was HCV NS5BΔ21 polymerase genotype J4 (1b).

Figure 12:
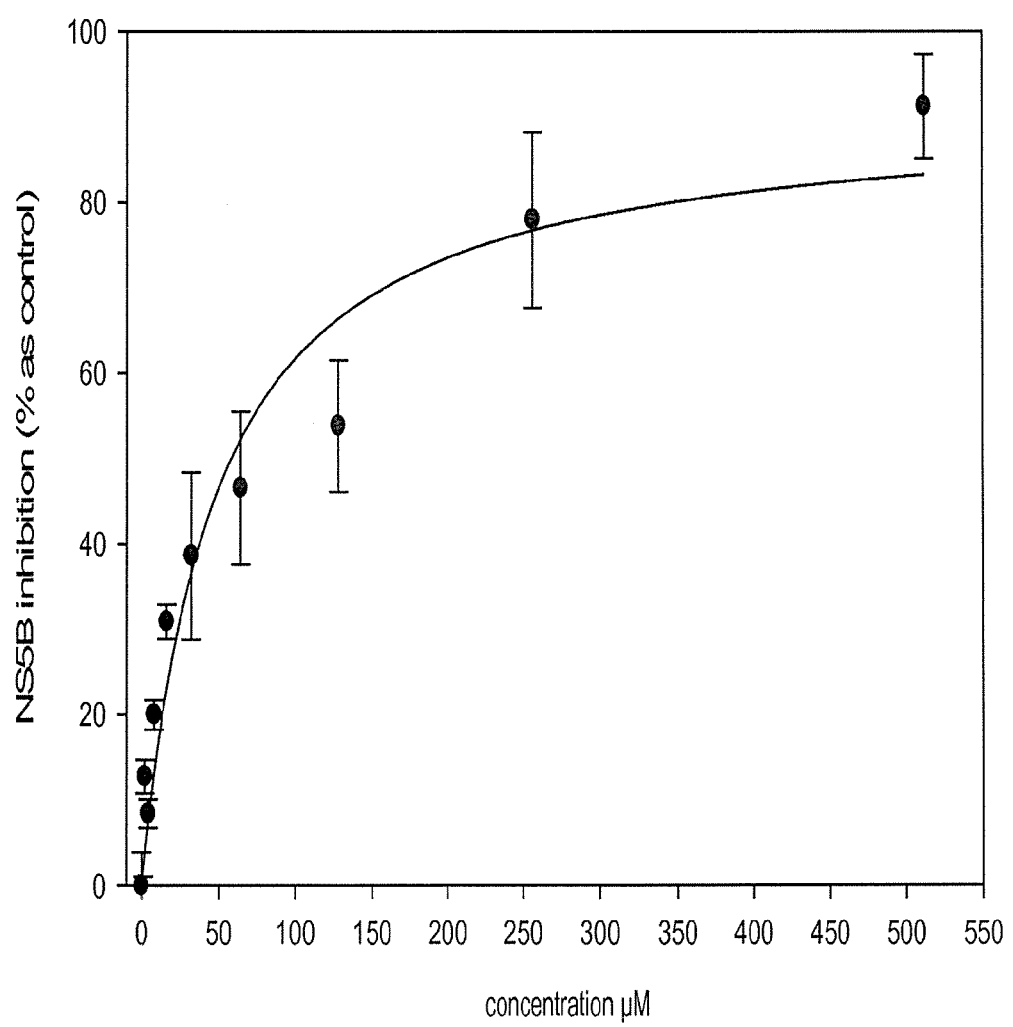
FIG. 12 shows data generated from in-vitro NS5B inhibition study for silibinin bis(hydrogensuccinate).

FIG. 11 shows the data generated for the six purified constituents of silymarin (i.e. silibinin A, silibinin B, isosilibinin A, isosilibinin B, silichristin, and silidianin). FIG. 12 shows the respective data for the silibinin ester. The silibinin ester revealed most efficient.

The $IC_{50}$ value of the silibinin ester was determined from the dose-response curve of two measurements. The determined $IC_{50}$ value was 47±14 µM. Curves were fitted to data points and $IC_{50}$ values were interpolated from the resulting curves using SigmaPlot 8.0 software.

The invention claimed is:

1. A method of treating hepatitis C comprising intravenously administering to a subject in need thereof a medicament comprising silibinin C2',3-bis(hydrogensuccinate) or a physiologically acceptable salt thereof as a silibinin component,
    wherein the medicament contains the silibinin component in a dose of at least 20 mg/kg, based on the body weight of the patient as an equivalent dose based on silibinin, and wherein the medicament essentially contains no silidianin, no silicristin, and no isosilibinin.

2. The method according to claim 1, wherein the medicament contains no other constituent of silymarin besides the silibinin component.

3. The method according to claim 1, wherein the medicament contains the silibinin component in a dose of at least 50 mg/kg, based on the body weight of the patient as an equivalent dose based on silibinin.

4. The method according to claim 1, wherein the medicament comprises a further pharmaceutical in addition to the silibinin component.

5. The method according to claim 4, wherein the further pharmaceutical is selected from the group consisting of arginine glutamate, citiolone, epomediol, ornithine oxoglurate, tidiacicarginine, myoinositol, methionine and N-acetylmethionine, choline, ornithine aspartate, cianidanol, tiopronine, betaine, cyanocobalamin, leucine, levulose, aciclovir, idoxuridine, vidarabine, ribavirin, ganciclovir, famciclovir, valaciclovir, cidofovir, penciclovir, valganciclovir, brivudine, interferon alfa, interferon beta, interferon gamma, interferon alfa-2a, interferon alfa-2b, interferon alfa-n1, interferon beta-1a, interferon beta-1b, interferon alfacon-1, peginterferon alfa-2b, peginterferon alfa-2a and interferon gamma 1b.

6. The method according to claim 1, wherein the medicament is administered to reduce the viral load in hepatitis patients.

7. The method according to claim 1, wherein the medicament is administered to treat viral hepatitis in a patient who will undergo or has undergone liver transplantation.

8. The method according to claim 1, wherein the medicament is administered to treat viral hepatitis in a patient who does not respond to therapy comprising ribavirin plus interferon.

9. The method according to claim 1, wherein after administering the medicament, another pharmaceutical is administered to the subject in need thereof.

10. The method according to claim 1, wherein the medicament is administered as a part of a sequential treatment, where the medicament is initially administered for a first period, and subsequently another pharmaceutical is administered for a second period.

11. The method according to claim 10, wherein the first period comprises at least 2 days.

12. The method as claimed in claim 9, wherein the pharmaceutical is selected from the group consisting of arginine glutamate, silymarin, citiolone, epomediol, ornithine oxoglurate, tidiacicarginine, myoinositol, methionine and N-acetylmethionine, choline, ornithine aspartate, cianidanol, tiopronine, betaine, cyanocobalamin, leucine, levulose, aciclovir, idoxuridine, vidarabine, ribavirin, ganciclovir, famciclovir, valaciclovir, cidofovir, penciclovir, valganciclovir, brivudine, interferon alfa, interferon beta, interferon gamma, interferon alfa-2a, interferon alfa-2b, interferon alfa-n1, interferon beta-1a, interferon beta-1b, interferon alfacon-1, peginterferon alfa-2b, peginterferon alfa-2a and interferon gamma 1b.

13. The method according to claim 9, wherein the pharmaceutical is administered orally to the subject in need thereof.

* * * * *